(12) United States Patent
Ichikawa et al.

(10) Patent No.: US 11,567,034 B2
(45) Date of Patent: Jan. 31, 2023

(54) GAS SENSOR SET AND METHOD OF MEASURING CONCENTRATIONS OF A PLURALITY OF TARGET COMPONENTS WITHIN A GAS TO BE MEASURED

(71) Applicant: NGK INSULATORS, LTD., Aichi (JP)

(72) Inventors: Daichi Ichikawa, Nagoya (JP); Yuichiro Kondo, Obu (JP); Nobuhiko Mori, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 0 days.

(21) Appl. No.: 17/205,189

(22) Filed: Mar. 18, 2021

(65) Prior Publication Data
US 2021/0293743 A1  Sep. 23, 2021

(30) Foreign Application Priority Data
Mar. 19, 2020 (JP) .............................. JP2020-049883

(51) Int. Cl.
*G01N 27/409* (2006.01)
*F01N 11/00* (2006.01)
*F01N 3/20* (2006.01)
*G01N 27/41* (2006.01)
*G01N 33/00* (2006.01)
*G01N 27/419* (2006.01)

(52) U.S. Cl.
CPC .......... *G01N 27/409* (2013.01); *F01N 3/208* (2013.01); *F01N 11/007* (2013.01); *G01N 27/41* (2013.01); *G01N 27/419* (2013.01); *G01N 33/0037* (2013.01); *G01N 33/0054* (2013.01); *F01N 2560/021* (2013.01); *F01N 2560/026* (2013.01)

(58) Field of Classification Search
CPC combination set(s) only.
See application file for complete search history.

(56) References Cited

U.S. PATENT DOCUMENTS

| | | | |
|---|---|---|---|
| 5,480,535 A * | 1/1996 | Kondo | G01N 27/417 204/426 |
| 6,136,170 A * | 10/2000 | Inoue | G01N 27/4075 204/426 |
| 2005/0241136 A1* | 11/2005 | Wu | G01N 27/4077 29/592.1 |
| 2009/0020422 A1* | 1/2009 | A | G01N 27/125 204/406 |
| 2017/0315106 A1* | 11/2017 | Bahrami | B01J 37/0215 |
| 2018/0252673 A1* | 9/2018 | Wang | G01N 27/4073 |
| 2019/0128833 A1 | 5/2019 | Nakagaki | |
| 2019/0137441 A1* | 5/2019 | Nakagaki | G01N 33/0037 |

FOREIGN PATENT DOCUMENTS

WO        2017/222002 A1      12/2017

* cited by examiner

*Primary Examiner* — Binh Q Tran
(74) *Attorney, Agent, or Firm* — Mattingly & Malur, PC

(57) ABSTRACT

A first gas sensor having a first sensor element includes a first protective cover that protects the first sensor element, and a second gas sensor having a second sensor element includes a second protective cover that protects the second sensor element. The first protective cover is coated with an oxidation catalyst for one target component from among a plurality of target components, and the second protective cover is coated with an inert catalyst for the one target component.

15 Claims, 17 Drawing Sheets

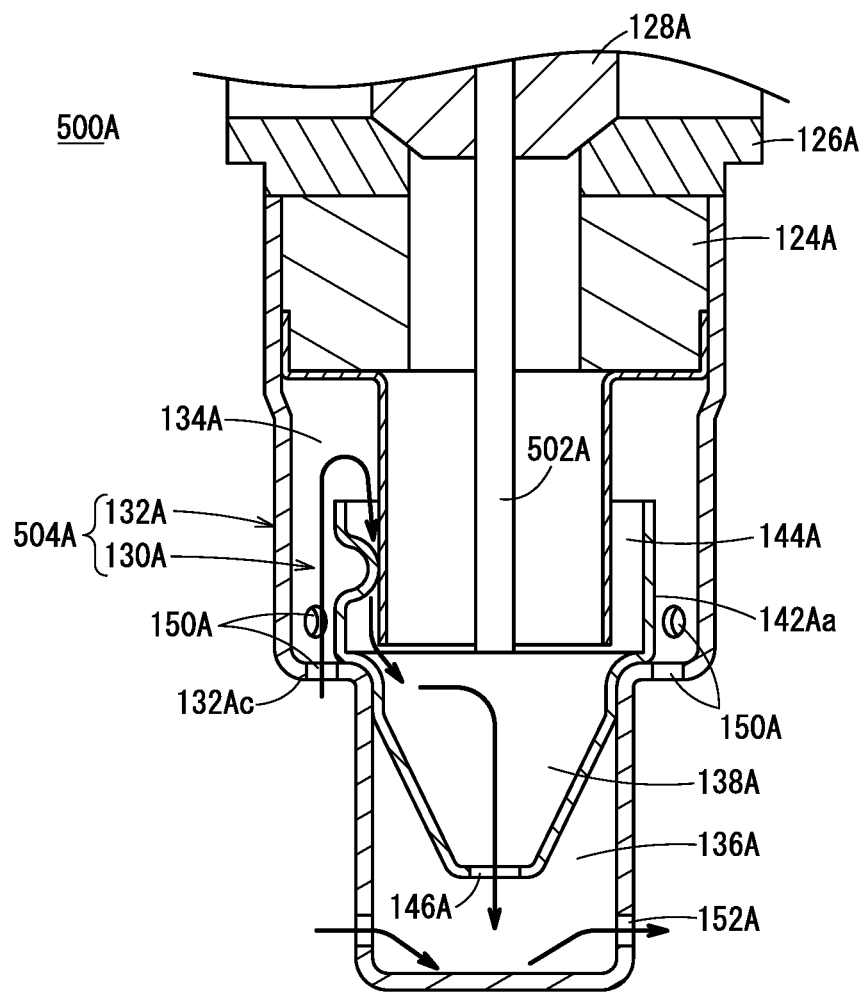

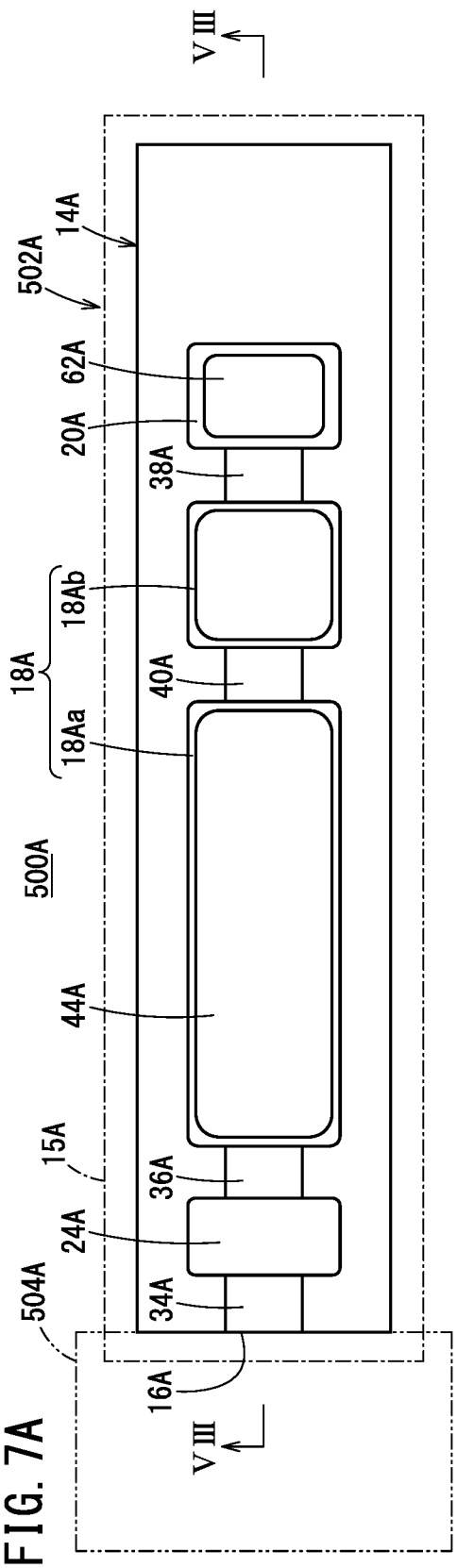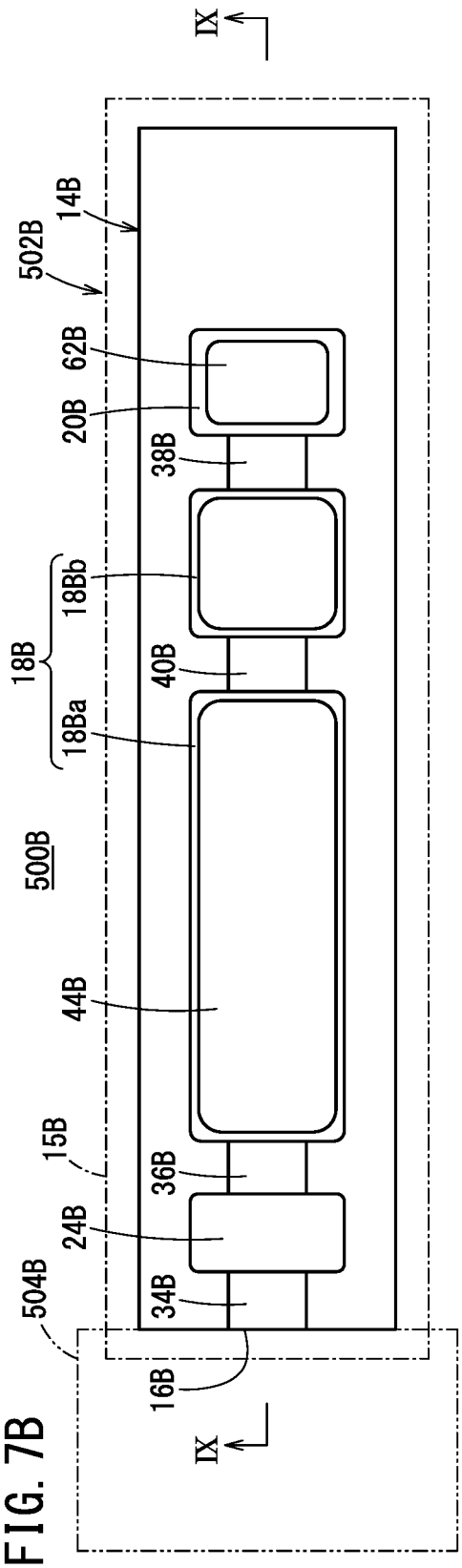

FIG. 13

[TABLE 1]

| | NO | NH3 | SENSOR CELL 2 | SENSOR CELL 1 | SENSOR CELL 2 - SENSOR CELL 1 |
|---|---|---|---|---|---|
| [1] | 0 | 100 | 2.428 | 2.126 | 0.302 |
| | 0 | 75 | 1.822 | 1.595 | 0.226 |
| | 0 | 50 | 1.216 | 1.065 | 0.151 |
| | 0 | 25 | 0.609 | 0.534 | 0.075 |
| | 0 | 0 | 0.003 | 0.003 | 0.000 |
| [2] | 100 | 0 | 2.137 | 1.997 | 0.140 |
| | 75 | 0 | 1.604 | 1.498 | 0.105 |
| | 50 | 0 | 1.070 | 1.000 | 0.070 |
| | 25 | 0 | 0.537 | 0.501 | 0.035 |
| | 0 | 0 | 0.003 | 0.003 | 0.000 |
| [3] | 100 | 0 | 2.137 | 1.997 | 0.140 |
| | 80 | 17.6 | 2.137 | 1.972 | 0.165 |
| | 60 | 35.2 | 2.137 | 1.947 | 0.190 |
| | 40 | 52.8 | 2.137 | 1.922 | 0.215 |
| | 20 | 70.4 | 2.137 | 1.897 | 0.240 |
| | 0 | 88.0 | 2.137 | 1.871 | 0.266 |
| [4] | 50 | 0.0 | 1.070 | 1.000 | 0.070 |
| | 40 | 8.8 | 1.070 | 0.987 | 0.083 |
| | 30 | 17.6 | 1.070 | 0.975 | 0.095 |
| | 20 | 26.4 | 1.070 | 0.962 | 0.108 |
| | 10 | 35.2 | 1.070 | 0.950 | 0.120 |
| | 0 | 44.0 | 1.070 | 0.937 | 0.133 |
| [5] | 25 | 0 | 0.537 | 0.501 | 0.035 |
| | 20 | 4.4 | 0.537 | 0.495 | 0.041 |
| | 15 | 8.8 | 0.537 | 0.489 | 0.048 |
| | 10 | 13.2 | 0.537 | 0.483 | 0.054 |
| | 5 | 17.6 | 0.537 | 0.476 | 0.060 |
| | 0 | 22.0 | 0.537 | 0.470 | 0.066 |

FIG. 14

[TABLE 2]

|  | NO | NH3 | SENSOR CELL 2 | SENSOR CELL 1 | SENSOR CELL 2 - SENSOR CELL 1 |
|---|---|---|---|---|---|
| [CONFIRMED] | 60 | 35.0 | 2.132 | 1.942 | 0.190 |
|  | 30 | 18.0 | 1.080 | 0.983 | 0.096 |
|  | 10 | 13.0 | 0.532 | 0.478 | 0.053 |

GAS SENSOR SET AND METHOD OF MEASURING CONCENTRATIONS OF A PLURALITY OF TARGET COMPONENTS WITHIN A GAS TO BE MEASURED

CROSS-REFERENCE TO RELATED APPLICATION

This application is based upon and claims the benefit of priority from Japanese Patent Application No. 2020-049883 filed on Mar. 19, 2020, the contents of which are incorporated herein by reference.

BACKGROUND OF THE INVENTION

Field of the Invention

The present invention relates to a gas sensor set in which an oxygen ion conductive solid electrolyte is used, and a method of measuring concentrations of a plurality of target components within a gas to be measured.

Description of the Related Art

Conventionally, gas sensors have been proposed which measure concentrations of a plurality of target components such as nitrogen oxide (NO) and ammonia ($NH_3$) and the like that coexist in the presence of oxygen, such as in an exhaust gas.

For example, in International Publication No. WO 2017/222002, a gas sensor is disclosed in which, in an oxygen ion conductive solid electrolyte, a preliminary vacant chamber, a main vacant chamber, an auxiliary vacant chamber, and a measurement vacant chamber which are partitioned by diffusion resistance members are provided, together with pumping electrodes being disposed in each of the respective chambers. With such a gas sensor, the progression or stoppage of an oxidation reaction of $NH_3$ into NO taking place inside the preliminary vacant chamber is switched by switching between driving (ON) or stopping (OFF) of a preliminary pump cell of the preliminary vacant chamber. In addition, the gas concentrations of $NH_3$ and NO are measured on the basis of a change in a pumping current (referred to hereinafter as a measurement pump current Ip3) of a measurement electrode inside the measurement vacant chamber, which occurs due to a difference in the diffusion rate of $NH_3$ and NO from the preliminary vacant chamber into the main vacant chamber.

SUMMARY OF THE INVENTION

In the gas sensor described in International Publication No. WO 2017/222002, the measurement pump current Ip3 is acquired while switching is carried out at regular intervals between ON or OFF of the preliminary pump cell of the preliminary vacant chamber. Therefore, a problem arises in that accuracy is lowered due to lengthening of the switching cycle, and accuracy is also lowered due to low sensitivity.
<Deterioration in Accuracy due to Lengthening of the Switching Cycle>

In addition to the $O_2$ concentration in the preliminary pump vacant chamber, the respective gas concentrations of each of the vacant chambers, the state quantity of the pump current, and the like, differ between when the preliminary pump cell is turned ON and when it is turned OFF. Stated otherwise, at a time of switching of the preliminary pump cell, the measurement pump current Ip3 settles to a steady value, after having been involved with a time delay due to gas diffusion resistance, electrode reaction resistance, and control of the pump voltage. Therefore, in order to acquire the measurement pump current Ip3on when turned ON and the measurement pump current Ip3off when turned OFF, it is necessary to wait for a time until settling to the steady state after switching of the preliminary pump cell has taken place, and the switching cycle must be set to a certain length. During the switching cycle, cases may occur in which the concentrations of $NOx/NH_3$ fluctuate, which leads to a concern that the accuracy in measuring the $NOx/NH_3$ concentrations may decrease. More specifically, from the fact that the switching cycle of the preliminary pump cell is lengthened, a problem arises in that a variation in the concentrations when the preliminary pump cell is turned ON and when it is turned OFF becomes large, and the accuracy in calculating the concentrations is lowered.
<Deterioration in Accuracy due to Low Sensitivity>

The $NH_3$ concentration is calculated from a difference ($=\Delta Ip3$) between the measurement pump current Ip3on when turned ON and the measurement pump current Ip3off when turned OFF. The value of $\Delta Ip3$ (=$NH_3$ sensitivity) with respect to a certain $NH_3$ concentration is about 20% of the value of Ip3off (=NO sensitivity) with respect to the same concentration of NO. On the other hand, upon detecting the measurement pump currents Ip3on and Ip3off, a noise component which is generated in both of the current values is of about the same degree, and therefore, the S/N ratio of the $NH_3$ sensitivity is about 20% of the S/N ratio of the NO sensitivity. Therefore, the accuracy in calculating the $NH_3$ concentration is also about 20% of the accuracy in calculating the NO concentration (an error of 5 times), and a problem arises in that the accuracy in calculating the concentrations is lowered.

The present invention has been devised taking into consideration the aforementioned problems, and has the object of providing a gas sensor which is capable of preventing both a decrease in the accuracy of calculating the concentrations due to lengthening of the switching cycle, and a decrease in the accuracy of calculating the concentrations due to low sensitivity.

A first aspect of the present invention is characterized by a gas sensor set configured to detect a plurality of target components, and including at least two gas sensors installed in an exhaust pipe, wherein:

among the at least two gas sensors, at least one first gas sensor includes a first sensor element including a first sensor cell formed in a first structural body made up from at least an oxygen ion conductive solid electrolyte;

among the at least two gas sensors, at least one second gas sensor includes a second sensor element including a second sensor cell formed in a second structural body made up from at least an oxygen ion conductive solid electrolyte;

an oxidation catalyst for one target component from among a plurality of target components is coated over a range corresponding to at least a gas introducing portion of the first sensor element; and an inert catalyst for the one target component is coated over a range corresponding to at least a gas introducing portion of the second sensor element.

A second aspect of the present invention is characterized by a gas sensor set configured to detect a plurality of target components, and including a gas sensor installed in an exhaust pipe;

wherein the gas sensor includes:

a structural body made up from at least an oxygen ion conductive solid electrolyte;

a sensor element including a first sensor cell formed in the structural body and having a first gas introducing portion, and a second sensor cell formed in the structural body and having a second gas introducing portion; and a protective cover configured to protect at least the first gas introducing portion and the second gas introducing portion of the sensor element; and on the protective cover:

an oxidation catalyst for one target component from among the plurality of target components is coated over a range corresponding to at least the first gas introducing portion of the sensor element; and an inert catalyst for the one target component is coated over a range corresponding to at least the second gas introducing portion of the sensor element.

A third aspect of the present invention is characterized by a method of measuring concentrations of a plurality of target components within a gas to be measured by a gas sensor set wherein:

the gas sensor set includes a first sensor cell and a second sensor cell;

each of the first sensor cell and the second sensor cell is equipped, in a direction in which a gas is introduced, at least with a gas introduction port, a first diffusion rate control member, a first chamber, a second diffusion rate control member, a second chamber, a third diffusion rate control member, and a measurement chamber;

the measurement chamber of the first sensor cell includes a first measurement pump cell; and the measurement chamber of the second sensor cell includes a second measurement pump cell;

the method including the steps of:

acquiring a concentration of a second target component, based on a difference between a current value flowing to the first measurement pump cell and a current value flowing to the second measurement pump cell;

acquiring a total concentration of the first target component and a second target component, by the current value flowing to the second measurement pump cell; and acquiring a concentration of the first target component by subtracting the concentration of the second target component from the total concentration.

In accordance with the first aspect, the second aspect, or the third aspect of the present invention, it is possible to prevent both a decrease in the accuracy of calculating the concentrations due to lengthening of the switching cycle, and a decrease in the accuracy of calculating the concentrations due to low sensitivity. Further, it is possible to accurately measure over a prolonged time period the concentration of a non-combusted component such as exhaust gas, and a plurality of components (for example, NO and $NH_3$) that coexist in the presence of oxygen.

The above and other objects, features, and advantages of the present invention will become more apparent from the following description when taken in conjunction with the accompanying drawings, in which a preferred embodiment of the present invention is shown by way of illustrative example.

BRIEF DESCRIPTION OF THE DRAWINGS

FIG. 3 is an explanatory diagram showing operations of a first protective cover in the first gas sensor;

FIG. 7A is a cross-sectional view (a cross-sectional view taken along line VIIA-VIIA in FIG. 8: dashed lines omitted) showing a structural example of a first gas sensor;

FIG. 7B is a cross-sectional view (a cross-sectional view taken along line VIIB-VIIB in FIG. 9: dashed lines omitted) showing a structural example of a second gas sensor;

FIG. 13 is an explanatory diagram (Table 1) showing the map utilized by the gas sensor set in the form of a table;

FIG. 14 is an explanatory diagram (Table 2) showing measurement results in the form of a table in order to confirm the certainty of the map;

DESCRIPTION OF THE PREFERRED EMBODIMENTS

Preferred embodiments of a gas sensor set, and a method of measuring concentrations of a plurality of target components within a gas to be measured according to the present invention will be presented and described below with reference to the accompanying drawings.

First, a basic exemplary configuration example and measurement principles of a gas sensor set (hereinafter referred to as a first gas sensor set 1000A) according to the first embodiment will be described below.

Figure 1A:
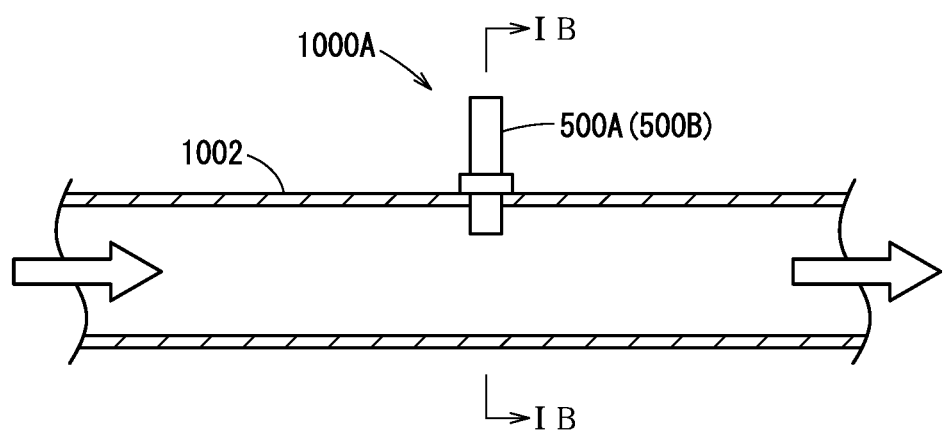
FIG. 1A is a schematic configuration diagram showing a first gas sensor set.
Figure 1B:
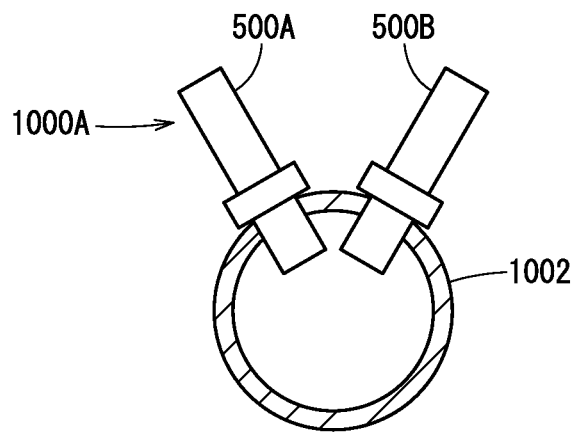
FIG. 1B is a cross-sectional view showing a structural example of the first gas sensor set (a cross-sectional view taken along IB-IB line in FIG. 1A: dashed lines omitted).

As shown in FIGS. 1A and 1B, the first gas sensor set 1000A includes a first gas sensor 500A and a second gas sensor 500B installed, for example, in an exhaust pipe 1002, which is an exhaust path from an engine of a non-illustrated vehicle, and serve to detect the concentrations of at least two from among gas components such as NOx, $NH_3$, and $O_2$ contained in an exhaust gas serving as a gas to be measured which is discharged from the engine.

As shown in FIG. 1B, the first gas sensor 500A and the second gas sensor 500B are fixed to the interior of the exhaust pipe 1002, in a state in which central axes of the first gas sensor 500A and the second gas sensor 500B lie perpendicular to a flow direction of the gas to be measured inside the exhaust pipe 1002. The respective central axes of the first gas sensor 500A and the second gas sensor 500B may be fixed to the interior of the exhaust pipe 1002, in a state of being perpendicular to the flow direction of the gas to be measured inside the exhaust pipe 1002, while in addition, being inclined at a predetermined angle (for example, 45°) with respect to the vertical direction.

Figure 2A:
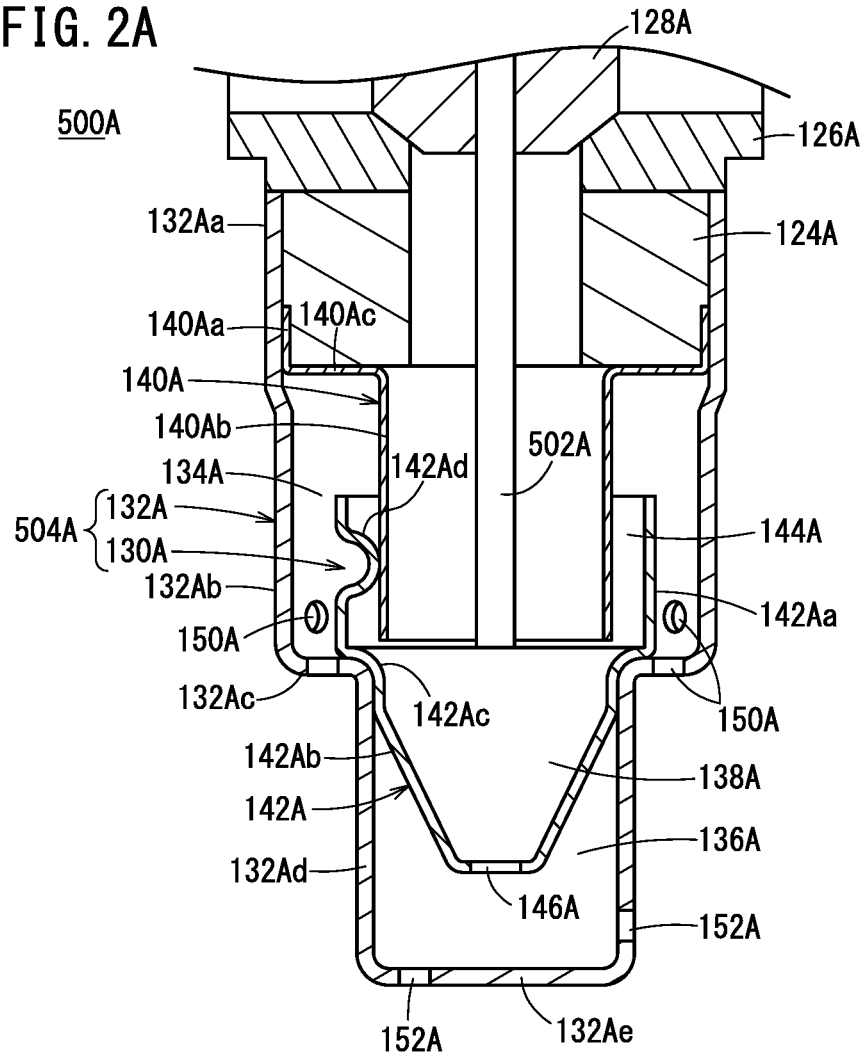
FIG. 2A is a vertical cross-sectional view showing a structural example of a first gas sensor (a cross-sectional view taken along line IIA-IIA in FIG. 2B)
Figure 2B:
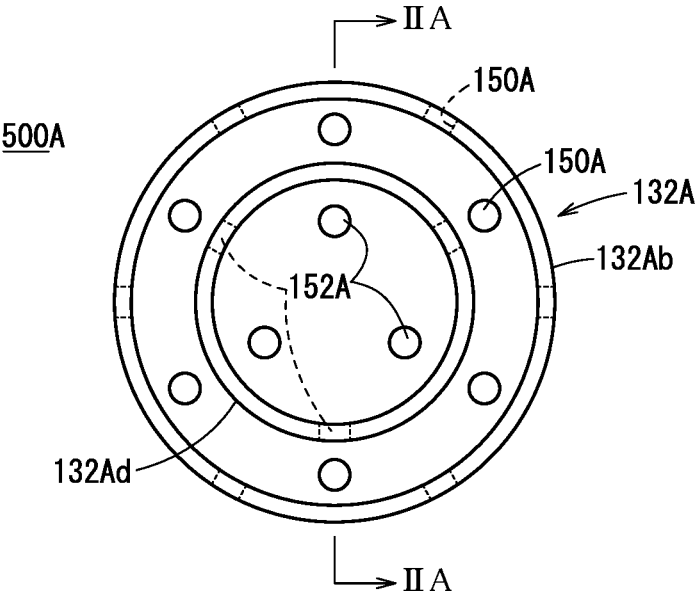
FIG. 2B is a view showing the first gas sensor as viewed from below.

As shown in FIGS. 2A and 2B, the first gas sensor 500A is equipped with a first sensor element 502A which has a function of detecting a predetermined gas concentration within the gas to be measured, a first protective cover 504A that covers a periphery around the first sensor element 502A, a housing 124A, a fixing member 126A, and a sensor supporting member 128A. The fixing member 126A is formed in a cylindrical shape, and is joined to the exhaust pipe 1002 (see FIG. 1A) by welding, fastening by screws, or the like. The housing 124A is a metal member formed in a cylindrical shape, and is joined to the fixing member 126A. The first protective cover 504A is attached to the outer periphery of the housing 124A. The sensor supporting member 128A is joined to a central portion of the fixing member 126A, and supports a proximal end part of the first sensor element 502A. Consequently, the first gas sensor 500A is fixed inside the exhaust pipe 1002 (see FIG. 1A). Moreover, the direction in which the gas to be measured flows inside the exhaust pipe 1002 may be either of the directions in FIG. 2A.

The first protective cover 504A is arranged in surrounding relation to the periphery of the first sensor element 502A. The first protective cover 504A includes a bottomed tubular first inner side cover 130A that covers the distal end of the first sensor element 502A, and a first outer side cover 132A that covers the first inner side cover 130A. Further, a first gas chamber 134A and a second gas chamber 136A are formed in a portion surrounded by the first inner side cover 130A and the first outer side cover 132A. A sensor element chamber 138A is formed on an inner side of the first inner side cover 130A. The first protective cover 504A is formed of a metal, for example, stainless steel or the like.

The first inner side cover 130A includes an inner side member 140A and an outer side member 142A. The inner side member 140A includes a cylindrical large-diameter section 140Aa, a cylindrical small-diameter section 140Ab of a smaller diameter than the large-diameter section 140Aa, and a stepped portion 140Ac that interconnects the large-diameter section 140Aa and the small-diameter section 140Ab. The inner side member 140A is separated from the outer side of the first sensor element 502A, and is disposed in surrounding relation to a side portion of the first sensor element 502A.

The outer side member 142A includes a cylindrically shaped tubular section 142Aa formed with a larger diameter than the small-diameter section 140Ab of the inner side member 140A, a conical section 142Ab provided on a distal end side of the tubular section 142Aa, and an intermediate section 142Ac disposed between the tubular section 142Aa and the conical section 142Ab. The tubular section 142Aa is arranged in covering relation to the outer side of the small-diameter section 140Ab, whereby a gap 144A is formed between the small-diameter section 140Ab and the tubular section 142Aa. Further, a part of the tubular section 142Aa is projected diametrically inward, and abuts against the small-diameter section 140Ab of the inner side member 140A through a plurality of protruding portions 142Ad. The intermediate section 142Ac is formed in a shape along an inner circumferential surface of a stepped portion 132Ac of the first outer side cover 132A, and the intermediate section 142Ac abuts against the first outer side cover 132A. The conical section 142Ab is formed in a conical shape with a diameter decreasing toward the distal end side, and is disposed in covering relation to the distal end side of the first sensor element 502A. More specifically, a gas introducing portion of the first sensor element 502A is arranged toward the sensor element chamber 138A. A distal end side of the conical section 142Ab is formed in a flat shape, and a circular element chamber outlet 146A, which enables communication between the second gas chamber 136A and the sensor element chamber 138A, is formed in a distal end part of the conical section 142Ab.

A proximal end part of the first inner side cover 130A is fixed to the housing 124A at the large-diameter section 140Aa of the inner side member 140A. A gap between the inner side member 140A and the outer side member 142A of the first inner side cover 130A forms a flow passage for the gas to be measured to the first sensor element 502A.

The first outer side cover 132A comprises a cylindrical large diameter section 132Aa, a cylindrical body section 132Ab formed integrally on the distal end side of the large diameter section 132Aa, and a stepped portion 132Ac formed on the distal end side of the body section 132Ab, and which is reduced in diameter in a radial inward direction. Further, the first outer side cover 132A comprises a cylindrical distal end portion 132Ad that extends from the stepped portion 132Ac to the distal end side, and a distal end surface 132Ae which is formed so as to close the distal end side of the distal end portion 132Ad. The first outer side cover 132A is fixed to the housing 124A at the large diameter section 132Aa.

On the body section 132Ab and the stepped portion 132Ac, six first gas chamber through holes 150A, which enable communication between the exhaust pipe 1002 (see FIGS. 1A and 1B) and the first gas chamber 134A, are arranged respectively at intervals of roughly 60° in the circumferential direction as shown in FIG. 2B. Further, on the distal end portion 132Ad and the distal end surface 132Ae, a plurality of second gas chamber through holes 152A are provided, which enable communication between the exhaust gas pipe and the second gas chamber 136A. Thereamong, three of the second gas chamber through holes 152A are arranged on the distal end surface 132Ae at intervals of 120° in the circumferential direction. Three of the second gas chamber through holes 152A are also arranged on the distal end surface 132Ad at intervals of 120° in the circumferential direction. The gas to be measured (for example, an exhaust gas) flowing from the first gas chamber through holes 150A and the second gas chamber through holes 152A passes through the first gas chamber 134A, the second gas chamber 136A, and the sensor element chamber 138A of the first protective cover 504A, and is guided to the first sensor element 502A.

Furthermore, a $NH_3$ oxidation catalyst is coated on the inner surface of the first inner side cover 130A of the first gas sensor 500A. As an example of the coating for the $NH_3$ oxidation catalyst, there may be cited a Pt (platinum) coating having an oxidizing power with respect to $NH_3$. The range over which the $NH_3$ oxidation catalyst is coated is a range, shown in FIG. 2A, covering at least the gas introducing portion of the first sensor element 502A. Of course, the $NH_3$ oxidation catalyst may also be coated on the inner surface (a portion of the inner surface or the entirety of the inner surface) of the first inner side cover 130A, or alternatively, the $NH_3$ oxidation catalyst may be coated on the inner surface, or the outer surface, or the inner surface and the outer surface of the inner side member 140A.

Additionally, as shown in FIG. 3, the gas to be measured (for example, an exhaust gas) which has flowed into the first gas chamber 134A from the first gas chamber through holes 150A, is guided through the gap 144A to the sensor element chamber 138A. The gas to be measured flows out to the exterior through the element chamber outlet 146A, the second gas chamber 136A, and the second gas chamber through holes 152A.

More specifically, the first outer side cover 132A introduces the gas through the first gas chamber through holes 150A from a substantially intermediate portion in the lengthwise direction, and guides the gas rearwardly of the first inner side cover 130A. The first inner side cover 130A introduces the gas from the rear through a rear opening (the gap 144A), and guides the gas to the gas introducing portion of the first sensor element 502A. At this time, the introduced gas remains temporarily inside the sensor element chamber 138A, together with a portion of the gas being taken into the first sensor element 502A. Moreover, the gas that is introduced into the sensor element chamber 138A is guided to the side of the first outer side cover 132A through an opening (the element chamber outlet 146A).

Figure 4A:
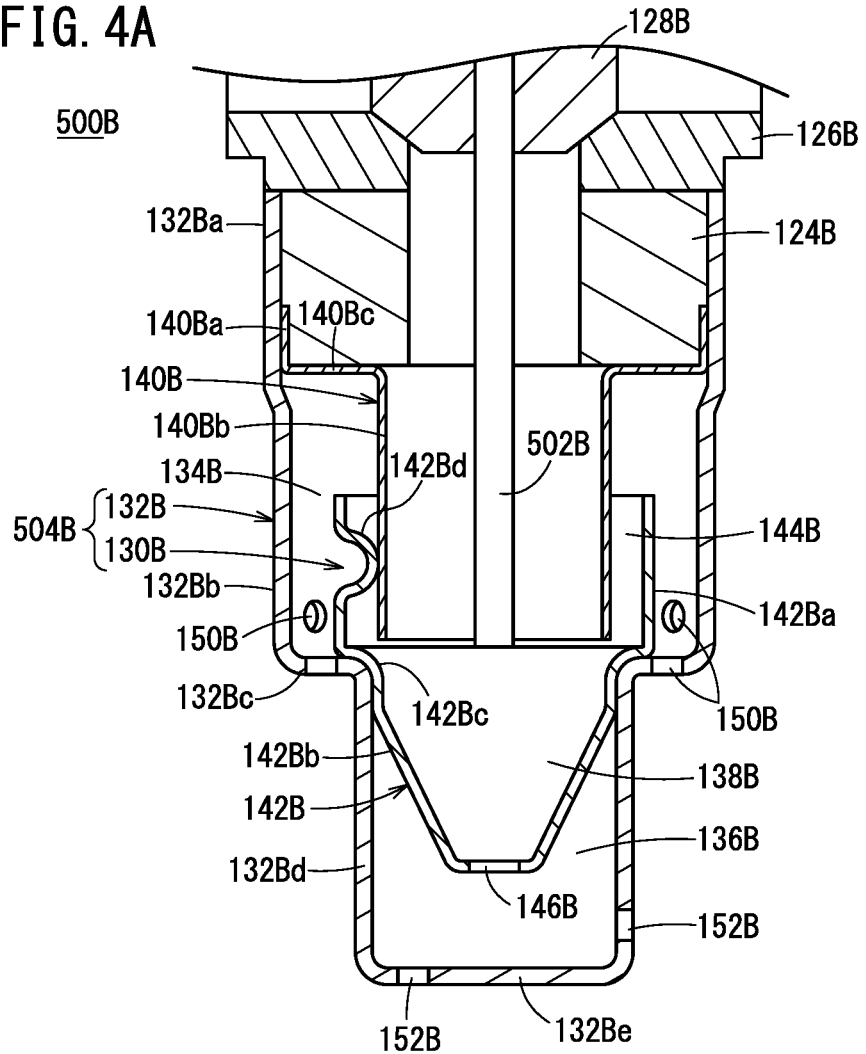
FIG. 4A is a vertical cross-sectional view showing a structural example of a second gas sensor (a cross-sectional view taken along line IVA-IVA in FIG. 4B)
Figure 4B:
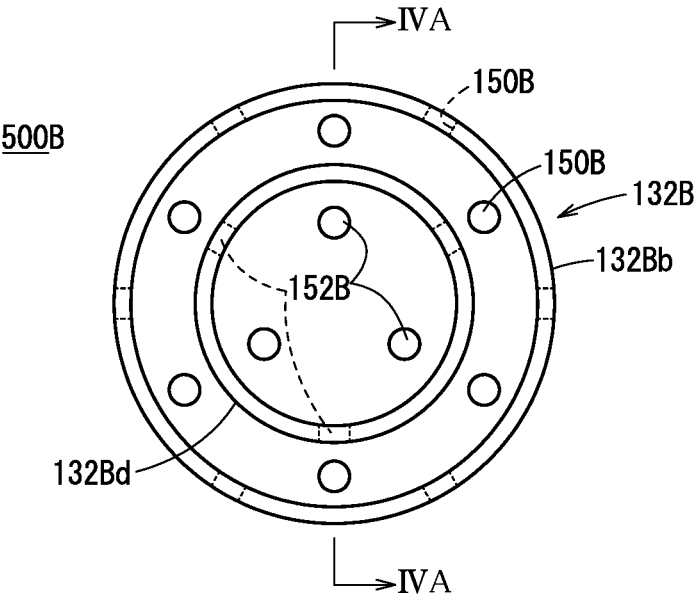
FIG. 4B is a view showing the second gas sensor as viewed from below.

As shown in FIGS. 4A and 4B, a second sensor element 502B and a second protective cover 504B of the second gas sensor 500B are configured in the same manner as the first sensor element 502A and the first protective cover 504A of the first gas sensor 500A described above. Accordingly, in FIGS. 4A and 4B, the letter "B" has been added to the reference numerals of the respective members, and duplicate description of such respective members is omitted.

The second protective cover 504B includes a second inner side cover 130B that protects at least a gas introducing portion of the second sensor element 502B, and a second outer side cover 132B that protects the second inner side cover 130B.

In addition, the second outer side cover 132B introduces the gas through a first gas chamber through holes 150B from a substantially intermediate portion in the lengthwise direction, and guides the gas rearwardly of the second inner side cover 130B. The second inner side cover 130B introduces the gas from the rear through a rear opening (the gap 144B), and guides the gas to the gas introducing portion of the second sensor element 502B. At this time, the introduced gas remains temporarily inside a sensor element chamber 138B, together with a portion of the gas being taken into the second sensor element 502B. Moreover, the gas that is introduced into the sensor element chamber 138B is guided to the side of the second outer side cover 132B through an opening (element chamber outlet 146B).

Furthermore, a $NH_3$ inert catalyst is coated on the inner surface of the second inner side cover 130B of the second gas sensor 500B. As an example of the coating for the $NH_3$ inert catalyst, there may be cited a CrN (chromium nitride) coating that is inert with respect to $NH_3$. The range over which the $NH_3$ inert catalyst is coated is a range, shown in FIG. 4A, covering at least the gas introducing portion of the second sensor element 502B. Of course, the $NH_3$ inert catalyst may also be coated on the inner surface (a portion of the inner surface or the entirety of the inner surface) of the second inner side cover 130B, or alternatively, the $NH_3$ inert catalyst may be coated on the inner surface, or the outer surface, or the inner surface and the outer surface of an inner side member 140B.

Figure 5A:
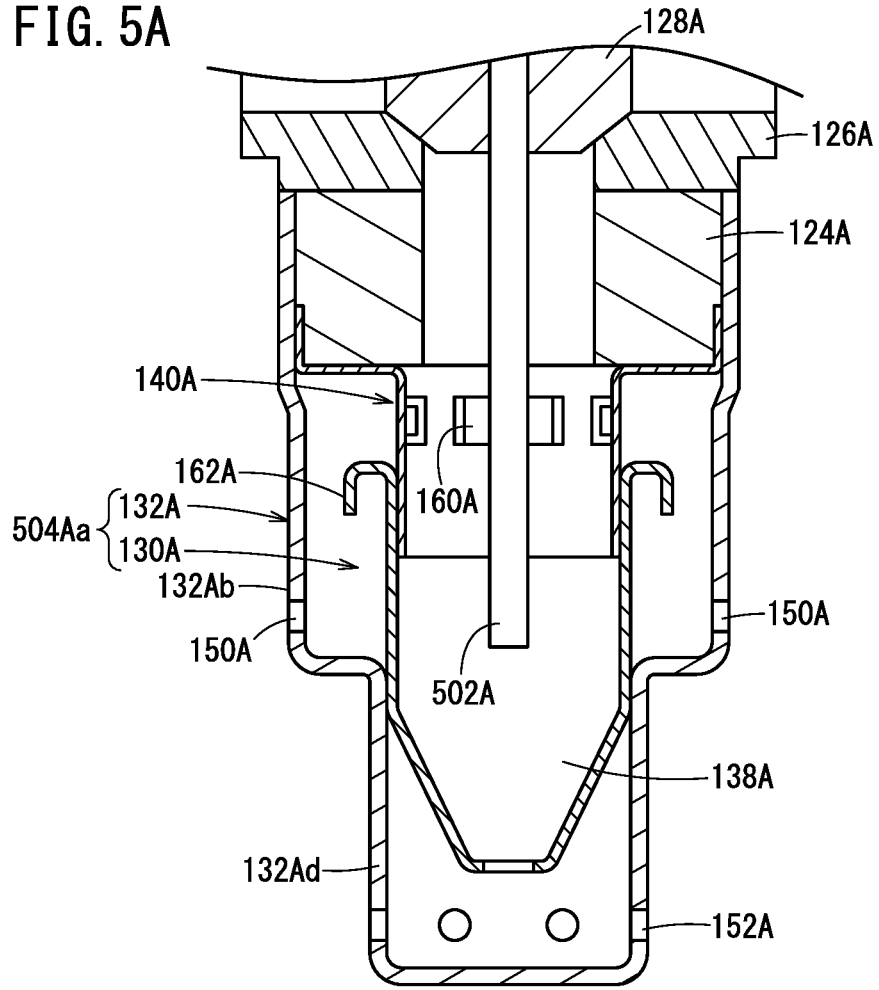
FIG. 5A is a vertical cross-sectional view (a cross-sectional view taken along line VA-VA in FIG. 5B) showing an exemplary configuration of a first protective cover according to another example.
Figure 5B:
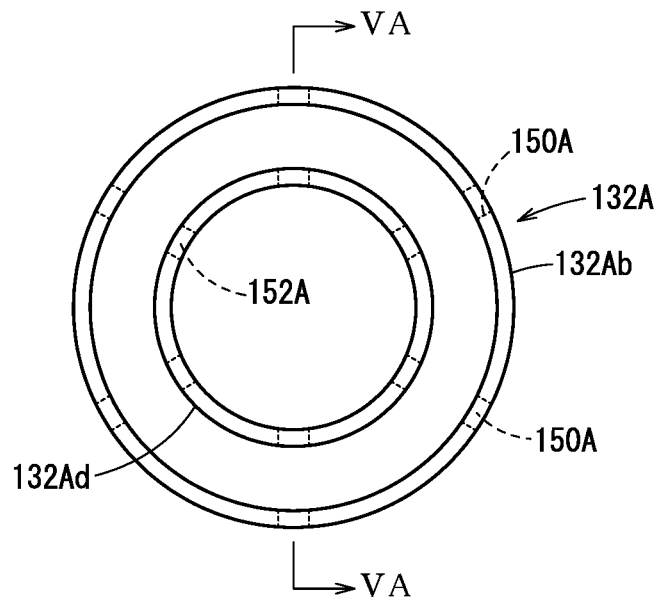
FIG. 5B is a view showing the first protective cover according to the other example as viewed from below.
Figure 6:
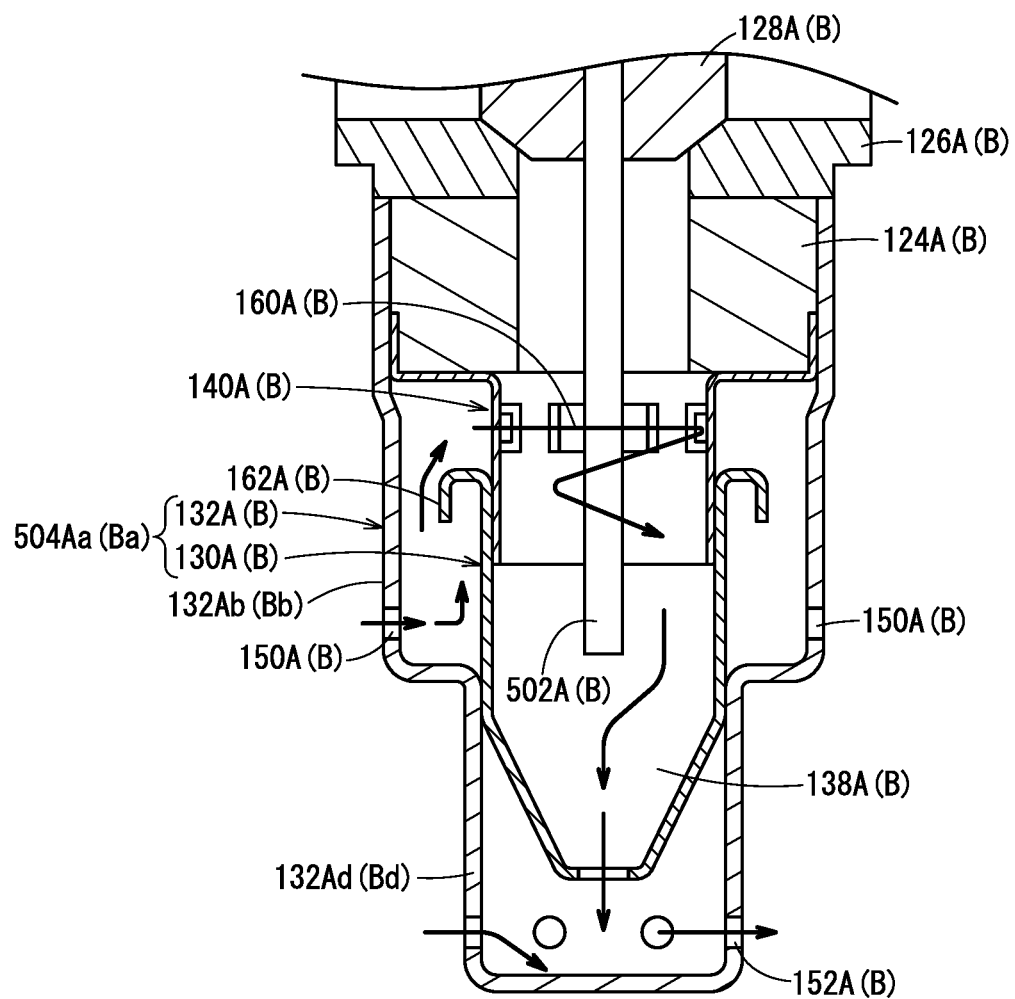
FIG. 6 is an explanatory diagram showing operations of a first protective cover according to another example.

For example, in the above-described first outer side cover 132A, the gas to be measured is delivered into the side of the sensor element chamber through a gap between the first inner side cover 130A and the inner side member 140A. Apart therefrom, a configuration may be provided, as shown in a first protective cover 504Aa of another example shown in FIGS. 5A, 5B, and 6. More specifically, without providing the above-described gap 144A (see FIG. 2A), a plurality of through holes 160A may be provided at a position that is closer to the housing 124A within the inner side member 140A. Through the through holes 160A, the gas to be measured is guided to the first sensor element 502A, and is delivered into the side of the sensor element chamber 138A through the gas introducing portion of the first sensor element 502A. Although not illustrated, the same features as those described above are also applied to the second protective cover 504B. Moreover, as shown in FIG. 6, a diffusion piece 162A, which is deformed into an inverted U-shape, may be provided at the rear end of the first inner side cover 130A. In accordance with this feature, the measurement gas that has entered into the gap between the first outer side cover 132A and the inner side member 140A is diffused or scattered, and is guided to the rear of the inner side member 140A.

Next, an exemplary configuration of a first gas sensor 500A and a second gas sensor 500B will be described with reference to FIGS. 7A to 11.

As shown in FIG. 7A, the first gas sensor 500A includes the first sensor element 502A. The first sensor element 502A includes a first structural body 14A made up from an oxygen ion conductive solid electrolyte, and a first sensor cell 15A formed in the first structural body 14A.

The first sensor cell 15A includes a first gas introduction port 16A into which a gas to be measured is introduced, a first oxygen concentration adjustment chamber 18A communicating with the first gas introduction port 16A, and a first measurement chamber 20A communicating with the first oxygen concentration adjustment chamber 18A. The first gas introduction port 16A, the first oxygen concentration adjustment chamber 18A, and the first measurement chamber 20A are formed inside the first structural body 14A.

The first oxygen concentration adjustment chamber 18A includes a first main adjustment chamber 18Aa in communication with the first gas introduction port 16A, and a first auxiliary adjustment chamber 18Ab in communication with the first main adjustment chamber 18Aa. The first measurement chamber 20A communicates with the first auxiliary adjustment chamber 18Ab.

Furthermore, the first sensor cell 15A includes a first diffusion resistance adjustment chamber 24A (a first chamber of the first sensor cell 15A) provided between the first gas introduction port 16A and the first main adjustment chamber 18Aa within the first structural body 14A, and which communicates with the first gas introduction port 16A.

Figure 8:
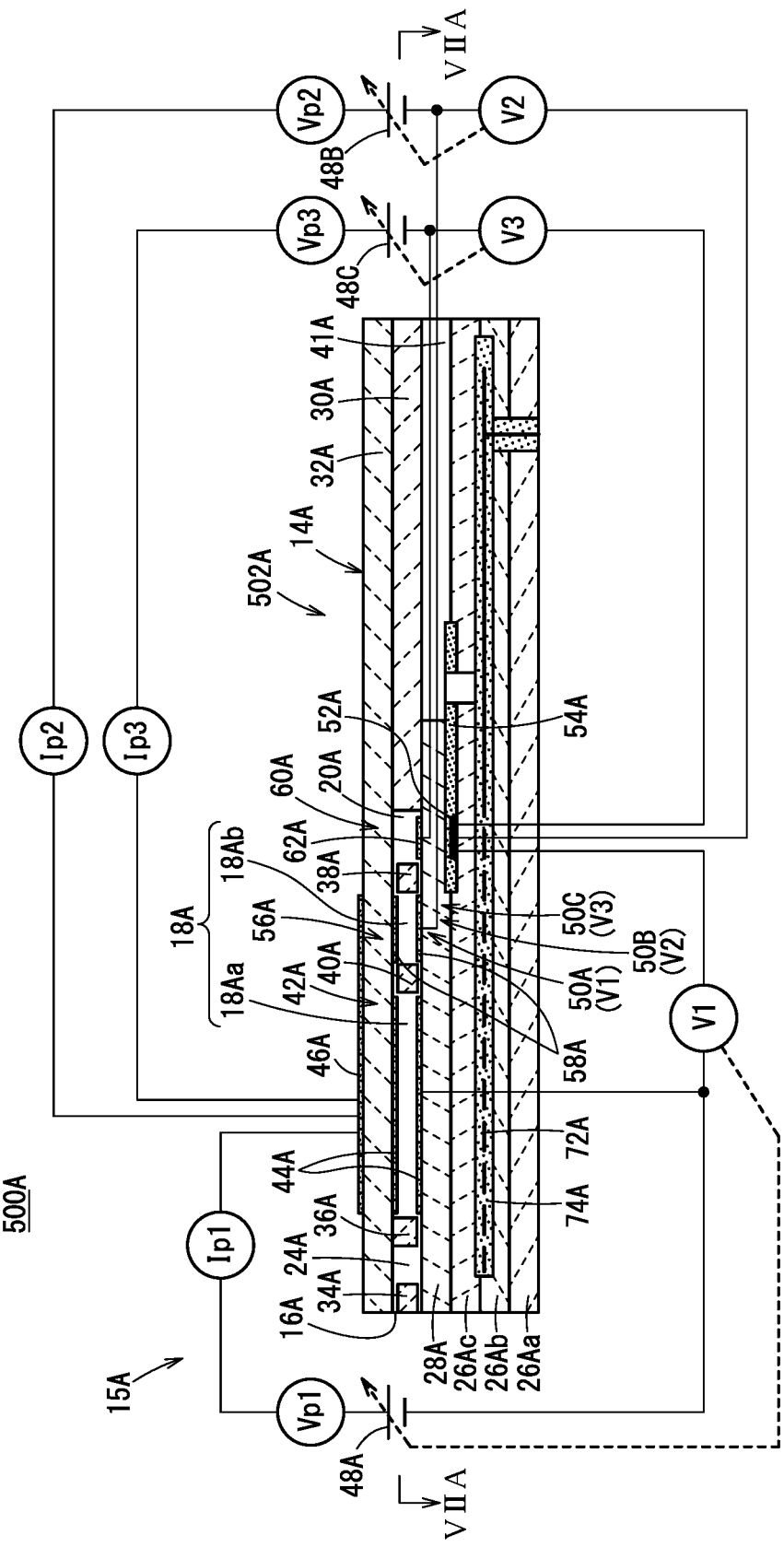
FIG. 8 is a cross-sectional view (a cross-sectional view taken along line VIII-VIII in FIG. 7A) showing a structural example of a first sensor cell in the first gas sensor.

More specifically, as shown in FIG. 8, the first structural body 14A is constituted by six layers including a first substrate layer 26Aa, a second substrate layer 26Ab, a third substrate layer 26Ac, a first solid electrolyte layer 28A, a first spacer layer 30A, and a second solid electrolyte layer 32A, which are stacked in this order from a lower side as viewed in the drawing. The respective layers are composed respectively of an oxygen ion conductive solid electrolyte layer such as zirconia ($ZrO_2$) or the like.

In the first sensor cell 15A, between a lower surface of the second solid electrolyte layer 32A and an upper surface of the first solid electrolyte layer 28A on a distal end side of the first sensor element 502A, there are provided the first gas introduction port 16A, a first diffusion rate control member 34A, the first diffusion resistance adjustment chamber 24A, a second diffusion rate control member 36A, the first oxygen concentration adjustment chamber 18A, a third diffusion rate control member 38A, and the first measurement chamber 20A. Further, a fourth diffusion rate control member 40A is provided between the first main adjustment chamber 18Aa and the first auxiliary adjustment chamber 18Ab that make up the first oxygen concentration adjustment chamber 18A.

The first gas introduction port 16A, the first diffusion rate control member 34A, the first diffusion resistance adjustment chamber 24A, the second diffusion rate control member 36A, the first main adjustment chamber 18Aa, the fourth diffusion rate control member 40A, the first auxiliary adjustment chamber 18Ab, the third diffusion rate control member 38A, and the first measurement chamber 20A are formed adjacent to each other in a manner communicating in this order. A portion from the first gas introduction port 16A leading to the first measurement chamber 20A may also be referred to as a first gas flow section.

The first gas introduction port 16A, the first diffusion resistance adjustment chamber 24A, the first main adjustment chamber 18Aa, the first auxiliary adjustment chamber 18Ab, and the first measurement chamber 20A are internal spaces provided by 0 out the first spacer layer 30A. Any of the first diffusion resistance adjustment chamber 24A, the first main adjustment chamber 18Aa, the first auxiliary adjustment chamber 18Ab, and the first measurement chamber 20A is arranged in a manner so that respective upper parts thereof are defined by a lower surface of the second solid electrolyte layer 32A, respective lower parts thereof are defined by an upper surface of the first solid electrolyte layer 28A, and respective side parts thereof are defined by side surfaces of the first spacer layer 30A.

On the other hand, as shown in FIG. 7B, a second sensor cell 15B includes a second gas introduction port 16B formed in a second structural body 14B and into which a gas to be measured is introduced, a second oxygen concentration adjustment chamber 18B formed inside the second structural body 14B and communicating with the second gas introduction port 16B, and a second measurement chamber 20B formed inside the second structural body 14B and communicating with the second oxygen concentration adjustment chamber 18B.

The second oxygen concentration adjustment chamber 18B includes a second main adjustment chamber 18Ba in communication with the second gas introduction port 16B, and a second auxiliary adjustment chamber 18Bb in communication with the second main adjustment chamber 18Ba. The second measurement chamber 20B communicates with the second auxiliary adjustment chamber 18Bb.

Furthermore, the second sensor cell 15B includes a second diffusion resistance adjustment chamber 24B (a first chamber of the second sensor cell 15B) provided between the second gas introduction port 16B and the second main adjustment chamber 18Ba within the second structural body 14B, and which communicates with the second gas introduction port 16B.

Figure 9:
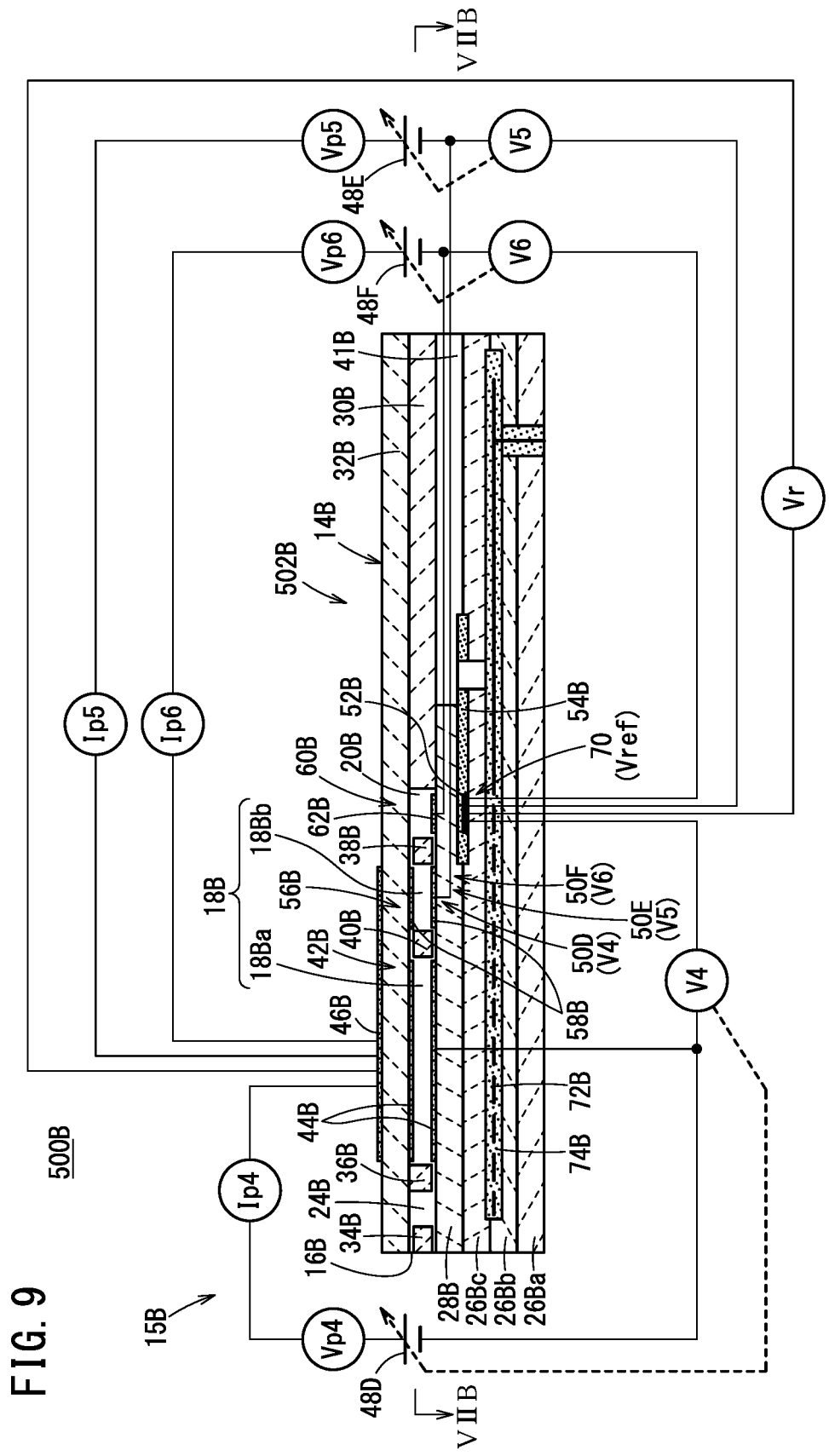
FIG. 9 is a cross-sectional view (a cross-sectional view taken along line IX-IX in FIG. 7B) showing a structural example of a second sensor cell in the second gas sensor.

More specifically, as shown in FIG. 9, the second structural body 14B is constituted by six layers including a first substrate layer 26Ba, a second substrate layer 26Bb, a third substrate layer 26Bc, a first solid electrolyte layer 28B, a second spacer layer 30B, and a second solid electrolyte layer 32B, which are stacked in this order from a lower side as viewed in the drawing. The respective layers are composed respectively of an oxygen ion conductive solid electrolyte layer such as zirconia ($ZrO_2$) or the like.

Between a lower surface of the second solid electrolyte layer 32B and an upper surface of the first solid electrolyte layer 28B on a distal end side of the second sensor element 502B, the second sensor cell 15B is equipped with the second gas introduction port 16B, a first diffusion rate control member 34B, the second diffusion resistance adjustment chamber 24B, a second diffusion rate control member 36B, the second oxygen concentration adjustment chamber 18B, a third diffusion rate control member 38B, and the second measurement chamber 20B. Further, a fourth diffusion rate control member 40B is provided between the second main adjustment chamber 18Ba and the second auxiliary adjustment chamber 18Bb that make up the second oxygen concentration adjustment chamber 18B.

The second gas introduction port 16B, the first diffusion rate control member 34B, the second diffusion resistance adjustment chamber 24B, the second diffusion rate control member 36B, the second main adjustment chamber 18Ba, the fourth diffusion rate control member 40B, the second auxiliary adjustment chamber 18Bb, the third diffusion rate control member 38B, and the second measurement chamber 20B are formed adjacent to each other in a manner communicating in this order. A portion from the second gas introduction port 16B leading to the second measurement chamber 20B may also be referred to as a second gas flow section.

The second gas introduction port 16B, the second diffusion resistance adjustment chamber 24B, the second main adjustment chamber 18Ba, the second auxiliary adjustment chamber 18Bb, and the second measurement chamber 20B are internal spaces provided by hollowing out the second spacer layer 30B. Any of the second diffusion resistance adjustment chamber 24B, the second main adjustment chamber 18Ba, the second auxiliary adjustment chamber 18Bb, and the second measurement chamber 20B is arranged in a manner so that respective upper parts thereof are defined by a lower surface of the second solid electrolyte layer 32B, respective lower parts thereof are defined by an upper surface of the first solid electrolyte layer 28B, and respective side parts thereof are defined by side surfaces of the second spacer layer 30B.

As shown in FIGS. 8 and 9, together with the first sensor cell 15A and the second sensor cell 15B, any of the first diffusion rate control members (34A and 34B), the third diffusion rate control members (38A and 38B), and the fourth diffusion rate control members (40A and 40B) are provided as two horizontally elongated slits (in which openings thereof have a longitudinal direction in a direction perpendicular to the drawing). The respective second diffusion rate control members (36A and 36B) are provided as one or two horizontally elongated slits (in which an opening thereof has a longitudinal direction in a direction perpendicular to the drawing).

Further, as shown in FIG. 8, concerning the first sensor cell 15A, a reference gas introduction space 41A is disposed between an upper surface of the third substrate layer 26Ac and a lower surface of the first spacer layer 30A, at a position that is farther from the distal end side than the first gas flow section. The reference gas introduction space 41A is an internal space in which an upper part thereof is defined by a lower surface of the first spacer layer 30A, a lower part thereof is defined by an upper surface of the third substrate layer 26Ac, and side parts thereof are defined by side surfaces of the first solid electrolyte layer 28A. For example, oxygen or atmospheric air is introduced as a reference gas into the reference gas introduction space 41A.

The first gas introduction port 16A is a location that opens with respect to the external space, and the gas to be measured is drawn into the first sensor cell 15A from the external space through the first gas introduction port 16A.

The first diffusion rate control member 34A of the first sensor cell 15A is a location that imparts a predetermined diffusion resistance to the gas to be measured which is introduced from the first gas introduction port 16A into the first diffusion resistance adjustment chamber 24A.

The second diffusion rate control member 36A of the first sensor cell 15A is a location that imparts a predetermined diffusion resistance to the gas to be measured which is introduced from the first diffusion resistance adjustment chamber 24A into the first main adjustment chamber 18Aa.

The first main adjustment chamber 18Aa is provided as a space for the purpose of adjusting an oxygen partial pressure within the gas to be measured that is introduced from the first gas introduction port 16A. The oxygen partial pressure is adjusted by operation of a first main pump cell 42A.

The first main pump cell 42A comprises a first electrochemical pump cell (main electrochemical pumping cell), which is constituted by including a first main interior side pump electrode 44A, a first exterior side pump electrode 46A, and an oxygen ion conductive solid electrolyte which is sandwiched between the two pump electrodes. The first main interior side pump electrode 44A is provided substantially over the entire surface, respectively, of an upper surface of the first solid electrolyte layer 28A, a lower surface of the second solid electrolyte layer 32A, and side surfaces of the first spacer layer 30A that define the first main adjustment chamber 18Aa. The first exterior side pump electrode 46A is provided in a condition of being exposed to the external space on the upper surface of the second solid electrolyte layer 32A.

The first main pump cell 42A applies a first pump voltage Vp1 supplied from a first variable power source 48A for the first sensor cell 15A which is provided externally of the first sensor element 502A, and by allowing a first pump current Ip1 to flow between the first exterior side pump electrode 46A and the first main interior side pump electrode 44A, it is possible to pump oxygen in the interior of the first main adjustment chamber 18Aa into the external space, or alternatively, to pump oxygen in the external space into the first main adjustment chamber 18Aa.

Further, the first sensor cell 15A includes a first oxygen partial pressure detecting sensor cell 50A which is an electrochemical sensor cell. The first oxygen partial pressure detecting sensor cell 50A is constituted by the first main interior side pump electrode 44A, a first reference electrode 52A sandwiched between the first solid electrolyte layer 28A and an upper surface of the third substrate layer 26Ac, and an oxygen ion conductive solid electrolyte sandwiched between these electrodes. The first reference electrode 52A is an electrode having a substantially rectangular shape as viewed in plan, which is made from a porous cermet in the same manner as the first exterior side pump electrode 46A and the like. Further, around the periphery of the first reference electrode 52A, a first reference gas introduction layer 54A is provided, which is made from porous alumina and is connected to the first reference gas introduction space 41A. More specifically, the reference gas in the first reference gas introduction space 41A is introduced to the surface of the first reference electrode 52A via the first reference gas introduction layer 54A. The first oxygen partial pressure detecting sensor cell 50A generates a first electromotive force V1 between the first main interior side pump electrode 44A and the first reference electrode 52A, which is caused by the difference in oxygen concentration between the atmosphere inside the first main adjustment chamber 18Aa and the reference gas in the first reference gas introduction space 41A.

The first electromotive force V1 generated in the first oxygen partial pressure detecting sensor cell 50A changes depending on the oxygen partial pressure of the atmosphere existing in the first main adjustment chamber 18Aa. In accordance with the aforementioned first electromotive force V1, the first sensor cell 15A feedback-controls the first variable power source 48A of the first main pump cell 42A. Consequently, the first pump voltage Vp1, which is applied by the first variable power source 48A to the first main pump cell 42A, can be controlled in accordance with the oxygen partial pressure of the atmosphere in the first main adjustment chamber 18Aa.

The fourth diffusion rate control member 40A imparts a predetermined diffusion resistance to the gas to be measured, the oxygen concentration (oxygen partial pressure) of which is controlled by operation of the first main pump cell 42A in the first main adjustment chamber 18Aa, and is a location that guides the gas to be measured into the first auxiliary adjustment chamber 18Ab.

The first auxiliary adjustment chamber 18Ab is provided as a space for further carrying out adjustment of the oxygen partial pressure by a first auxiliary pump cell 56A, with respect to the gas to be measured which is introduced through the fourth diffusion rate control member 40A, after the oxygen concentration (oxygen partial pressure) has been adjusted beforehand in the first main adjustment chamber 18Aa. In accordance with this feature, the oxygen concentration inside the first auxiliary adjustment chamber 18Ab can be kept constant with high accuracy, and therefore, the first sensor cell 15A is made capable of measuring the NOx concentration with high accuracy.

The first auxiliary pump cell 56A is an electrochemical pump cell, and within the first structural body 14A, is constituted by a first auxiliary pump electrode 58A formed in facing relation to the first auxiliary adjustment chamber 18Ab, the above-described first exterior side pump electrode 46A, the first solid electrolyte layer 28A, and the second solid electrolyte layer 32A.

Moreover, in the same manner as the first main interior side pump electrode 44A, the first auxiliary pump electrode 58A is also formed using a material that weakens the reduction capability with respect to the NOx component within the gas to be measured.

The first auxiliary pump cell 56A, by applying a desired second pump voltage Vp2 between the first auxiliary pump electrode 58A and the first exterior side pump electrode 46A, is capable of pumping out oxygen within the atmosphere inside the first auxiliary adjustment chamber 18Ab into the external space, or alternatively, is capable of pumping in oxygen from the external space into the first auxiliary adjustment chamber 18Ab.

Further, in order to control the oxygen partial pressure within the atmosphere inside the first auxiliary adjustment chamber 18Ab, an electrochemical sensor cell, and more specifically, a second oxygen partial pressure detecting sensor cell 50B for controlling the first auxiliary pump, is constituted by the first auxiliary pump electrode 58A, the first reference electrode 52A, the second solid electrolyte layer 32A, the first spacer layer 30A, and the first solid electrolyte layer 28A.

Moreover, the first auxiliary pump cell 56A carries out pumping by a second variable power source 48B, the voltage of which is controlled based on a second electromotive force V2 detected by the second oxygen partial pressure detecting sensor cell 50B. Consequently, the oxygen partial pressure within the atmosphere inside the first auxiliary adjustment chamber 18Ab is controlled so as to become a low partial pressure that does not substantially influence the measurement of NOx.

Further, together therewith, a second pump current value Ip2 of the first auxiliary pump cell 56A is used so as to control the second electromotive force V2 of the second oxygen partial pressure detecting sensor cell 50B. More specifically, the second pump current Ip2 is input as a control signal to the second oxygen partial pressure detecting sensor cell 50B, and by controlling the second electromotive force V2, the gradient of the oxygen partial pressure within the gas to be measured, which is introduced through the fourth diffusion rate control member 40A into the first auxiliary adjustment chamber 18Ab, is controlled so as to remain constant at all times. Furthermore, if the first variable power source 48A of the first main pump cell 42A is feedback-controlled, in a manner so that the second pump current value Ip2 becomes constant, the accuracy of the oxygen partial pressure control within the first auxiliary adjustment chamber 18Ab is further improved. When the first sensor cell 15A is used as a NOx sensor, by the actions of the first main pump cell 42A and the first auxiliary pump cell 56A, the oxygen concentration inside the first auxiliary adjustment chamber 18Ab is maintained at a predetermined value with high accuracy for each of the respective conditions.

The third diffusion rate control member 38A imparts a predetermined diffusion resistance to the gas to be measured, the oxygen concentration (oxygen partial pressure) of which is controlled by operation of the first auxiliary pump cell 56A in the first auxiliary adjustment chamber 18Ab, and is a location that guides the gas to be measured into the first measurement chamber 20A.

In the first sensor cell 15A, measurement of the NOx concentration is primarily performed by operation of a first measurement pump cell 60A provided in the first measurement chamber 20A. The first measurement pump cell 60A is an electrochemical pump cell constituted by a first measurement electrode 62A, the first exterior side pump electrode 46A, the second solid electrolyte layer 32A, the first spacer layer 30A, and the first solid electrolyte layer 28A. The first measurement electrode 62A is provided, for example, directly on the upper surface of the first solid electrolyte layer 28A inside the first measurement chamber 20A, and is a porous cermet electrode made of a material whose reduction capability with respect to the NOx component within the gas to be measured is higher than that of the first main interior side pump electrode 44A. The first measurement electrode 62A also functions as a NOx reduction catalyst for reducing NOx existing within the atmosphere above the first measurement electrode 62A.

The first measurement pump cell 60A is capable of pumping out oxygen that is generated by decomposition of nitrogen oxide within the atmosphere around the periphery of the first measurement electrode 62A (inside the first measurement chamber 20A), and can detect the generated amount as a third pump current value Ip3, and more specifically, as a sensor output (a first current value Ip3) of the first sensor cell 15A.

Further, in order to detect the oxygen partial pressure around the periphery of the first measurement electrode 62A (inside the first measurement chamber 20A), an electrochemical sensor cell, and more specifically, a third oxygen partial pressure detecting sensor cell 50C for controlling the measurement pump, is constituted by the first solid electrolyte layer 28A, the first measurement electrode 62A, and the first reference electrode 52A. A third variable power source 48C is controlled based on a third electromotive force V3 detected by the third oxygen partial pressure detecting sensor cell 50C.

The gas to be measured, which is introduced into the first auxiliary adjustment chamber 18Ab, reaches the first measurement electrode 62A inside the first measurement chamber 20A through the third diffusion rate control member 38A, under a condition in which the oxygen partial pressure is controlled. Nitrogen oxide existing within the gas to be measured around the periphery of the first measurement electrode 62A is reduced to thereby generate oxygen. Then, the generated oxygen is subjected to pumping by the first measurement pump cell 60A. At this time, a third pump voltage Vp3 of the third variable power source 48C is controlled in a manner so that the third electromotive force V3 detected by the third oxygen partial pressure detecting sensor cell 50C becomes constant. The amount of oxygen generated around the periphery of the first measurement electrode 62A is proportional to the concentration of nitrogen oxide within the gas to be measured. Accordingly, the nitrogen oxide concentration within the gas to be measured can be calculated using the first current value Ip3 of the first measurement pump cell 60A. More specifically, the first measurement pump cell 60A measures the concentration of a specified component (NO) within the first measurement chamber 20A.

Furthermore, in the first sensor cell 15A, a first heater 72A is formed in a manner of being sandwiched from above and below between the second substrate layer 26Ab and the third substrate layer 26Ac. The first heater 72A generates heat by being supplied with power from the exterior through a non-illustrated heater electrode provided on a lower surface of the first substrate layer 26Aa. As a result of the heat generated by the first heater 72A, the oxygen ion conductivity of the solid electrolyte that constitutes the first sensor cell 15A is enhanced. The first heater 72A is embedded over the entire region of the first diffusion resistance adjustment chamber 24A and the first oxygen concentration adjustment chamber 18A, as well as the first measurement chamber 20A, whereby a predetermined location of the first sensor cell 15A can be heated and maintained at a predetermined temperature. Moreover, a first heater insulating layer 74A made of alumina or the like is formed on the upper and lower surfaces of the first heater 72A, for the purpose of obtaining electrical insulation thereof from the second substrate layer 26Ab and the third substrate layer 26Ac.

The first diffusion resistance adjustment chamber 24A also functions as a buffer space. More specifically, it is possible to cancel out fluctuations in the concentration of the gas to be measured, which are caused by pressure fluctuations of the gas to be measured in the external space (pulsations in the exhaust pressure, in the case that the gas to be measured is an exhaust gas of an automobile).

On the other hand, as shown in FIG. 9, the second sensor cell 15B includes a second main pump cell 42B, a second auxiliary pump cell 56B, a fourth oxygen partial pressure detecting sensor cell 50D, a fifth oxygen partial pressure detecting sensor cell 50E, and a sixth oxygen partial pressure detecting sensor cell 50F.

The second main pump cell 42B, in the same manner as the first main pump cell 42A, comprises a second electrochemical pump cell (main electrochemical pumping cell), which is constituted by including a second main interior side pump electrode 44B, a second exterior side pump electrode 46B, and an oxygen ion conductive solid electrolyte which is sandwiched between the two pump electrodes.

By applying a fourth pump voltage Vp4 supplied from a fourth variable power source 48D for the second sensor cell, and by allowing a fourth pump current Ip4 to flow between the second exterior side pump electrode 46B and the second main interior side pump electrode 44B, it is possible to pump oxygen in the interior of the second main adjustment chamber 18Ba into the external space, or alternatively, to pump oxygen in the external space into the second main adjustment chamber 18Ba.

The second auxiliary pump cell 56B, in the same manner as the above-described first auxiliary pump cell 56A, is an electrochemical pump cell, and within the second structural body 14B, is constituted by a second auxiliary pump electrode 58B formed in facing relation to the second auxiliary adjustment chamber 18Bb, the second exterior side pump electrode 46B, the first solid electrolyte layer 28B, and the second solid electrolyte layer 32B.

The second auxiliary pump cell 56B, by applying a desired fifth voltage Vp5 between the second auxiliary pump electrode 58B and the second exterior side pump electrode 46B, is capable of pumping out oxygen within the atmosphere inside the second auxiliary adjustment chamber 18Bb into the external space, or alternatively, is capable of pumping in oxygen from the external space into the second auxiliary adjustment chamber 18Bb.

The fourth oxygen partial pressure detecting sensor cell 50D, in the same manner as the first oxygen partial pressure detecting sensor cell 50A, is constituted by the second main interior side pump electrode 44B, a common second reference electrode 52B sandwiched between the first solid electrolyte layer 28B and an upper surface of the third substrate layer 26Bc, and an oxygen ion conductive solid electrolyte sandwiched between these electrodes.

The fourth oxygen partial pressure detecting sensor cell 50D generates a fourth electromotive force V4 between the second main interior side pump electrode 44B and the second reference electrode 52B, which is caused by the difference in oxygen concentration between the atmosphere inside the second main adjustment chamber 18Ba and the reference gas in a reference gas introduction space 41B.

The fourth electromotive force V4 generated in the fourth oxygen partial pressure detecting sensor cell 50D changes depending on the oxygen partial pressure of the atmosphere existing in the second main adjustment chamber 18Ba. In accordance with the aforementioned fourth electromotive force V4, the second sensor cell 15B feedback-controls the fourth variable power source 48D of the second main pump cell 42B. Consequently, the fourth pump voltage Vp4, which is applied by the fourth variable power source 48D to the second main pump cell 42B, can be controlled in accordance with the oxygen partial pressure of the atmosphere in the second main adjustment chamber 18Ba.

Further, in order to control the oxygen partial pressure within the atmosphere inside the second auxiliary adjustment chamber 18Bb, an electrochemical sensor cell, and more specifically, the fifth oxygen partial pressure detecting sensor cell 50E for controlling the second auxiliary pump, is constituted by the second auxiliary pump electrode 58B, the second reference electrode 52B, the second solid electrolyte layer 32B, the second spacer layer 30B, and the first solid electrolyte layer 28B.

The second auxiliary pump cell 56B carries out pumping by a fifth variable power source 48E, the voltage of which is controlled based on a fifth electromotive force V5 detected by the fifth oxygen partial pressure detecting sensor cell 50E. Consequently, the oxygen partial pressure within the atmosphere inside the second auxiliary adjustment chamber 18Bb is controlled so as to become a low partial pressure that does not substantially influence the measurement of NOx.

Further, together therewith, a fifth pump current value Ip5 of the second auxiliary pump cell 56B is used so as to control the fifth electromotive force V5 of the fifth oxygen partial pressure detecting sensor cell 50E. More specifically, the fifth pump current Ip5 is input as a control signal to the fifth oxygen partial pressure detecting sensor cell 50E, and by controlling the fifth electromotive force V5, the gradient of the oxygen partial pressure within the gas to be measured, which is introduced through the fourth diffusion rate control member 40B into the second auxiliary adjustment chamber 18Bb, is controlled so as to remain constant at all times. Furthermore, if the fourth variable power source 48D of the second main pump cell 42B is feedback-controlled, in a manner so that the fifth pump current value Ip5 becomes constant, the accuracy of the oxygen partial pressure control within the second auxiliary adjustment chamber 18Bb is further improved. When the second sensor cell 15B is used as a NOx sensor, by the actions of the second main pump cell 42B and the second auxiliary pump cell 56B, the oxygen concentration inside the second auxiliary adjustment chamber 18Bb is maintained at a predetermined value with high accuracy for each of the respective conditions.

The third diffusion rate control member 38B imparts a predetermined diffusion resistance to the gas to be measured, the oxygen concentration (oxygen partial pressure) of which is controlled by operation of the second auxiliary pump cell 56B in the second auxiliary adjustment chamber 18Bb, and is a location that guides the gas to be measured into the second measurement chamber 20B.

In the second sensor cell 15B, measurement of the NOx concentration is primarily performed by operation of a second measurement pump cell 60B provided in the second measurement chamber 20B. The second measurement pump cell 60B is an electrochemical pump cell constituted by a second measurement electrode 62B, the second exterior side pump electrode 46B, the second solid electrolyte layer 32B, the second spacer layer 30B, and the first solid electrolyte layer 28B. The second measurement electrode 62B is provided, for example, directly on the upper surface of the first solid electrolyte layer 28B inside the second measurement chamber 20B, and is a porous cermet electrode made of a material whose reduction capability with respect to the NOx component within the gas to be measured is higher than that of the second main interior side pump electrode 44B. The second measurement electrode 62B also functions as a NOx reduction catalyst for reducing NOx existing within the atmosphere above the second measurement electrode 62B.

The second measurement pump cell 60B is capable of pumping out oxygen that is generated by decomposition of nitrogen oxide within the atmosphere around the periphery of the second measurement electrode 62B (inside the second measurement chamber 20B), and can detect the generated amount as a sixth pump current value $Ip6$, and more specifically, as a sensor output (a second current value $Ip6$) of the second sensor cell 15B.

Further, in order to detect the oxygen partial pressure around the periphery of the second measurement electrode 62B (inside the second measurement chamber 20B), an electrochemical sensor cell, and more specifically, the sixth oxygen partial pressure detecting sensor cell 50F for controlling the measurement pump, is constituted by the first solid electrolyte layer 28B, the second measurement electrode 62B, and the second reference electrode 52B. A sixth variable power source 48F is controlled based on a sixth electromotive force $V6$ detected by the sixth oxygen partial pressure detecting sensor cell 50F.

The gas to be measured, which is introduced into the second auxiliary adjustment chamber 18Bb, reaches the second measurement electrode 62B inside the second measurement chamber 20B through the third diffusion rate control member 38B, under a condition in which the oxygen partial pressure is controlled. Nitrogen oxide existing within the gas to be measured around the periphery of the second measurement electrode 62B is reduced to thereby generate oxygen. Then, the generated oxygen is subjected to pumping by the second measurement pump cell 60B. At this time, a sixth voltage $Vp6$ of the sixth variable power source 48F is controlled in a manner so that the sixth electromotive force $V6$ detected by the sixth oxygen partial pressure detecting sensor cell 50F becomes constant. The amount of oxygen generated around the periphery of the second measurement electrode 62B is proportional to the concentration of nitrogen oxide within the gas to be measured. Accordingly, the nitrogen oxide concentration within the gas to be measured can be calculated using the sixth measurement pump current value $Ip6$ of the second measurement pump cell 60B. More specifically, the second measurement pump cell 60B measures the concentration of a specified component (NO) within the second measurement chamber 20B.

Further, the second sensor cell 15B includes an electrochemical oxygen detecting cell 70. The oxygen detecting cell 70 includes the second solid electrolyte layer 32B, the second spacer layer 30B, the first solid electrolyte layer 28B, the third substrate layer 26Bc, the second exterior side pump electrode 46B, and the second reference electrode 52B. In accordance with the electromotive force $Vref$ obtained by the oxygen detecting cell 70, it is possible to detect the oxygen partial pressure within the gas to be measured existing externally of the second sensor element 502B.

Further, in the second sensor cell 15B, a second heater 72B is formed similarly to the aforementioned first heater 72A, in a manner of being sandwiched from above and below between the second substrate layer 26Bb and the third substrate layer 26Bc. The second heater 72B is embedded over the entire region of the second diffusion resistance adjustment chamber 24B and the second oxygen concentration adjustment chamber 18B, and the second measurement chamber 20B, whereby a predetermined location of the second sensor cell 15B can be heated and maintained at a predetermined temperature. Moreover, a second heater insulating layer 74B made of alumina or the like is formed on the upper and lower surfaces of the second heater 72B, for the purpose of obtaining electrical insulation thereof from the second substrate layer 26Bb and the third substrate layer 26Bc.

The second diffusion resistance adjustment chamber 24B also functions as a buffer space. More specifically, it is possible to cancel out fluctuations in the concentration of the gas to be measured, which are caused by pressure fluctuations of the gas to be measured in the external space (pulsations in the exhaust pressure, in the case that the gas to be measured is an exhaust gas of an automobile).

Figure 10:
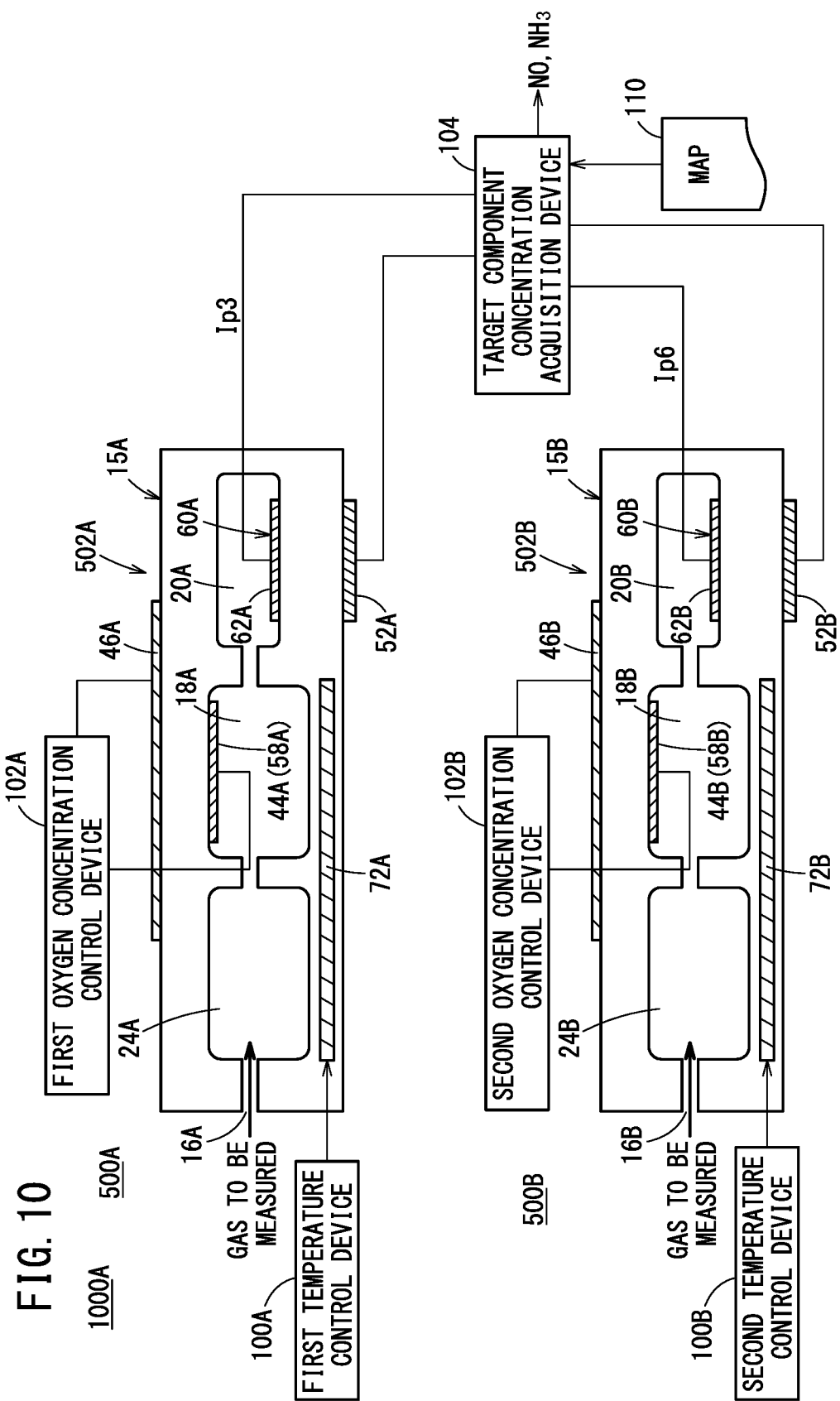
FIG. 10 is a configuration diagram schematically showing the first gas sensor set.

Furthermore, as shown schematically in FIG. 10, the first gas sensor set 1000A includes a first temperature control device 100A, a second temperature control device 100B, a first oxygen concentration control device 102A, a second oxygen concentration control device 102B, and a target component concentration acquisition device 104.

The first temperature control device 100A controls the supply of current to the first heater 72A of the first sensor element 502A, and thereby controls the temperature of the first sensor cell 15A. The second temperature control device 100B controls the supply of current to the second heater 72B of the second sensor element 502B, and thereby controls the temperature of the second sensor cell 15B.

The first oxygen concentration control device 102A controls the oxygen concentration inside the first oxygen concentration adjustment chamber 18A of the first sensor cell 15A. The second oxygen concentration control device 102B controls the oxygen concentration inside the second oxygen concentration adjustment chamber 18B of the second sensor cell 15B.

The target component concentration acquisition device 104 acquires the concentrations of the first target component (NO) and the second target component ($NH_3$), on the basis of the difference (amount of change $\Delta Ip$) between the first current value $Ip3$ flowing to the first measurement pump cell 60A of the first sensor cell 15A and the second current value $Ip6$ flowing to the second measurement pump cell 60B of the second sensor cell 15B, the second current value $Ip6$ (the total concentration), and a later-described map 110.

Moreover, the first temperature control device 100A, the second temperature control device 100B, the first oxygen concentration control device 102A, the second oxygen concentration control device 102B, and the target component concentration acquisition device 104 are constituted by one or more processors having, for example, one or a plurality of CPUs (central processing units), memory devices, and the like. The one or more processors are software-based functional units in which predetermined functions are realized, for example, by the CPUs executing programs stored in a storage device. Of course, the processors may be constituted by an integrated circuit such as an FPGA (Field-Programmable Gate Array), in which the plurality of processors are connected according to the functions thereof. Moreover, as noted above, the map 110 may be stored in advance in the storage device, which is one of the peripheral circuits of the gas sensor. Of course, the map 110, which is acquired (stored in the above-described storage device) through the communication means, may also be used.

The first temperature control device 100A and the second temperature control device 100B feedback-control the first heater 72A and the second heater 72B, on the basis of preset sensor temperature conditions, and the measured values from temperature sensors (not shown) that measure the respective temperature of the first sensor element 502A and the second sensor element 502B, whereby the respective temperatures of the first sensor element 502A and the second sensor element 502B are adjusted to temperatures in accordance with the above-described condition.

On the basis of the preset oxygen concentration condition inside the first oxygen concentration adjustment chamber 18A, and the second electromotive force V2 generated in the second oxygen partial pressure detecting sensor cell 50B (see FIG. 8), the first oxygen concentration control device 102A feedback-controls the first variable power source 48A, thereby adjusting the oxygen concentration inside the first oxygen concentration adjustment chamber 18A to a concentration in accordance with the above-described condition.

On the basis of the preset oxygen concentration condition inside the second oxygen concentration adjustment chamber 18B, and the fifth electromotive force V5 generated in the fifth oxygen partial pressure detecting sensor cell 50E (see FIG. 9), the second oxygen concentration control device 102B feedback-controls the fourth variable power source 48D, thereby adjusting the oxygen concentration inside the second oxygen concentration adjustment chamber 18B to a concentration in accordance with the above-described condition.

By such oxygen concentration control devices (102A and 102B) or the temperature control devices (100A and 100B), or alternatively, by the oxygen concentration control devices (102A and 102B) and the temperature control devices (100A and 100B), the first gas sensor set 1000A performs a control so as to convert the $NH_3$ into NO at a ratio suitable for measurement of $NH_3$, without causing decomposition of NO inside the first oxygen concentration adjustment chamber 18A of the first sensor element 502A and the second oxygen concentration adjustment chamber 18B of the second sensor element 502B.

Figure 11:
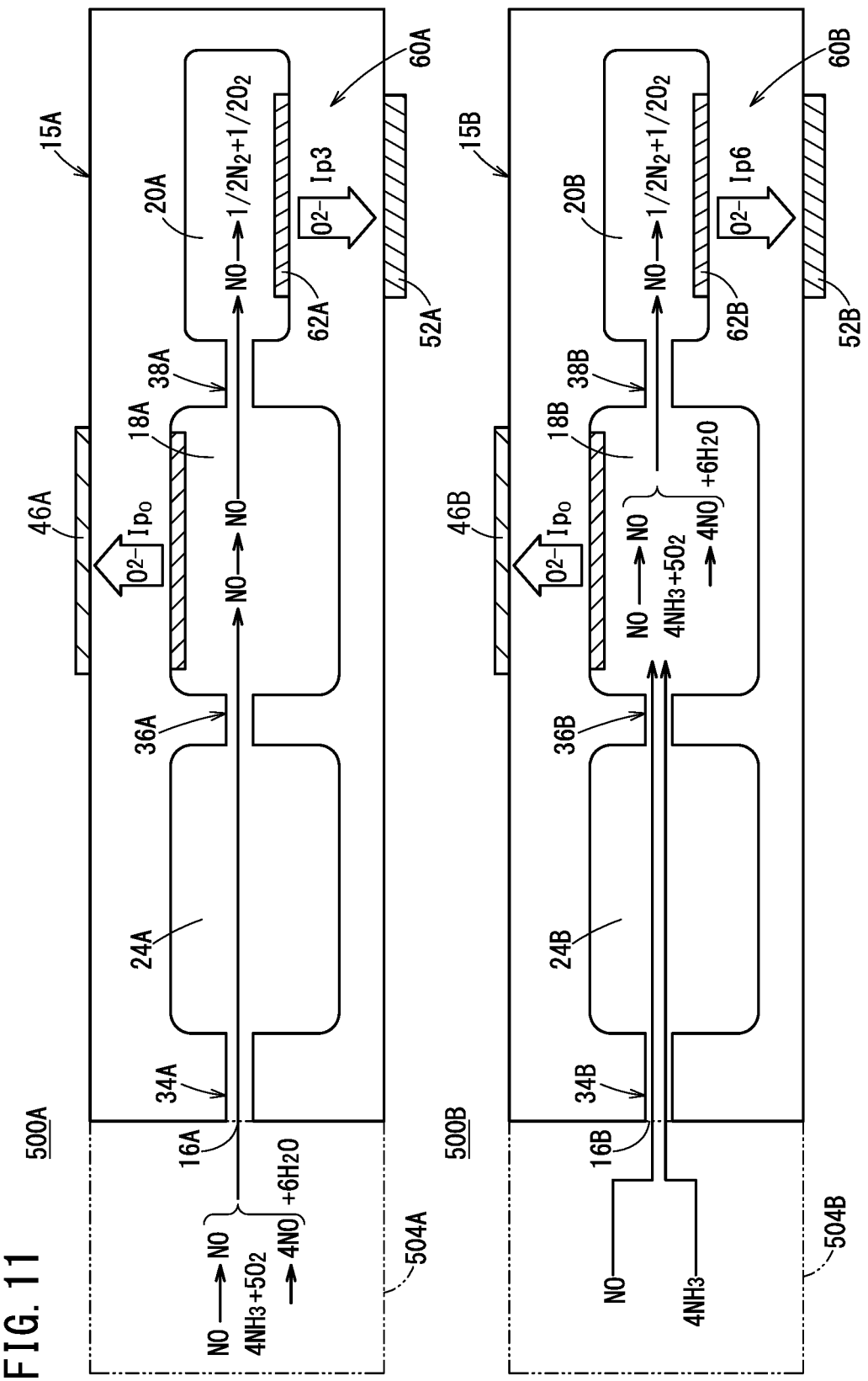
FIG. 11 is an explanatory diagram schematically showing reactions in a first protective cover of the first gas sensor, and inside a first diffusion resistance adjustment chamber, inside a first oxygen concentration adjustment chamber, and inside a first measurement chamber of the first sensor cell of the first gas sensor, as well as in a second protective cover of the second gas sensor, and inside a second diffusion resistance adjustment chamber, inside a second oxygen concentration adjustment chamber, and inside a second measurement chamber of the second sensor cell of the second gas sensor.

Processing operations of the first gas sensor set 1000A will be described with reference also to FIG. 11.

Initially, in the first gas sensor 500A, since the $NH_3$ oxidation catalyst is coated on the inner surface of the first protective cover 504A (see FIGS. 2A and 2B), the $NH_3$ that was introduced into the first protective cover 504A undergoes an oxidation reaction of $NH_3 \rightarrow NO$ in the interior of the first protective cover 504A, and almost all of the $NH_3$ that was introduced into the interior of the first protective cover 504A is converted into NO. More specifically, the $NH_3$ from the first diffusion rate controlling member 34A and thereafter move to the first measurement chamber 20A with a diffusion coefficient of NO of 1.8 $cm^2$/sec.

On the other hand, in the second gas sensor 500B, since the $NH_3$ inert catalyst is coated on the inner surface of the second protective cover 504B (see FIGS. 4A and 4B), the $NH_3$ that was introduced to the interior of the second protective cover 504B is introduced into the second sensor cell 15B via the second gas introduction port 16B without being converted into NO, and reaches the second oxygen concentration adjustment chamber 18B. In the second oxygen concentration adjustment chamber 18B, by operation of the second oxygen concentration control device 102B (see FIG. 10), a control is performed so as to convert all of the $NH_3$ into NO, and therefore, the $NH_3$ that has flowed into the second oxygen concentration adjustment chamber 18B causes an oxidation reaction of $NH_3 \rightarrow NO$ to occur inside the second oxygen concentration adjustment chamber 18B, and all of the $NH_3$ inside the second oxygen concentration adjustment chamber 18B is converted into NO. Accordingly, the $NH_3$ that was introduced through the second gas introduction port 16B passes through the first diffusion rate control member 34B and the second diffusion rate control member 36B at the $NH_3$ diffusion coefficient of 2.2 $cm^2$/sec, and after being converted into NO inside the second oxygen concentration adjustment chamber 18B, passes through the third diffusion rate control member 38B at the NO diffusion coefficient of 1.8 $cm^2$/sec, and moves into the adjacent second measurement chamber 20B.

More specifically, in the first sensor cell 15A, the location where the oxidation reaction of $NH_3$ takes place is inside the first protective cover 504A, and in the second sensor cell 15B, the location where the oxidation reaction of $NH_3$ takes place is inside the second oxygen concentration adjustment chamber 18B. Since NO and $NH_3$ each possess different diffusion coefficients, the difference between passing through the second diffusion rate control members (36A and 36B) with NO or passing therethrough with $NH_3$ corresponds to a difference in the amount of NO that flows into the first measurement chamber 20A and the second measurement chamber 20B. Such a feature brings about a difference between the first current value Ip3 of the first measurement pump cell 60A, and the second current value Ip6 of the second measurement pump cell 60B. However, significantly, the second current value Ip6 of the second measurement pump cell 60B corresponds to the total value of the $NH_3$ concentration and the NO concentration within the measurement gas.

Additionally, the amount of change ΔIp between the first current value Ip3 and the second current value Ip6 changes according to the $NH_3$ concentration within the gas to be measured. Therefore, the respective concentrations of NO and $NH_3$ can be obtained from the second current value Ip6 (the total concentration of NO and $NH_3$) that flows to the second measurement pump cell 60B, and the aforementioned amount of change ΔIp (the $NH_3$ concentration).

Figure 12:
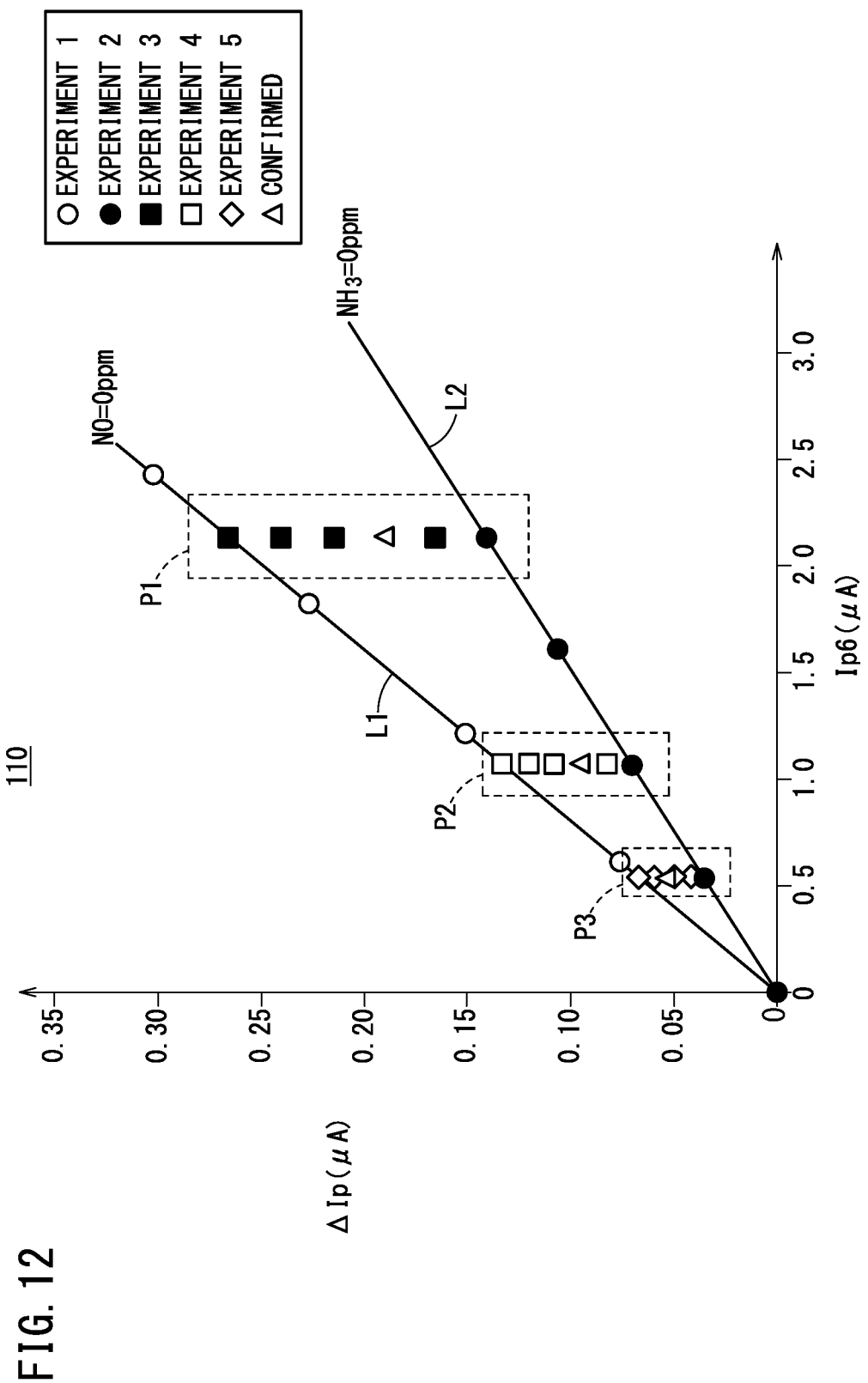
FIG. 12 is a graph showing a map utilized by the gas sensor set.

Accordingly, with the target component concentration acquisition device 104 (see FIG. 10), the respective concentrations of NO and $NH_3$ can be acquired on the basis of the amount of change ΔIp between the first current value Ip3 and the second current value Ip6, the second current value Ip6, and for example, the map 110 (see FIG. 10 and FIG. 12). When the map 110 is shown graphically, as shown in FIG. 12, a graph is produced in which the second current value Ip6 (μA) is set on the horizontal axis, and the amount of change ΔIp (μA) between the first current value Ip3 and the second current value Ip6 is set on the vertical axis. In FIG. 12, there are shown representatively a first characteristic line L1 and a second characteristic line L2, and a first plot group P1, a second plot group P2, and a third plot group P3 of the amount of change ΔIp, in which the NO concentration conversion values thereof pertain to a 100 ppm system, a 50 ppm system, and a 25 ppm system.

The first characteristic line L1 shows a characteristic, in relation to a case in which the NO concentration conversion value is 0 ppm, i.e., a case in which NO is not contained within the gas to be measured, for cases in which the $NH_3$ concentration conversion value is changed between 0 ppm, 25 ppm, 50 ppm, 75 ppm, and 100 ppm.

The second characteristic line L2 shows a characteristic, in relation to a case in which the $NH_3$ concentration conversion value is 0 ppm, i.e., a case in which $NH_3$ is not contained within the gas to be measured, for cases in which the NO concentration conversion value is changed between 0 ppm, 25 ppm, 50 ppm, 75 ppm, and 100 ppm.

When the graph of FIG. 12 is shown in the form of a table to facilitate understanding, the contents thereof are as shown in FIG. 13. The contents thereof can be determined, for example, by carrying out Experiments 1 to 5, which will be described later.

In the table of FIG. 13, the contents presented in the first section [1] correspond to the first characteristic line L1 of FIG. 12, and the contents presented in the second section [2] correspond to the second characteristic line L2 of FIG. 12. From a comparison of sections [1] and [2], it can be understood that $NH_3$ possesses a sensitivity that is 1.14 times that of NO. Such a feature is manifested on the basis of the difference in the diffusion coefficients of $NH_3$ and NO, and is determined by the temperature of the sensor element and the oxygen concentration within the internal space. Further, in the table of FIG. 13, the contents of the third section [3] correspond to the first plot group P1 of FIG. 12, the contents of the fourth section [4] correspond to the second plot group P2 of FIG. 12, and the contents of the fifth section [5] correspond to the third plot group P3 of FIG. 12.

In addition, referring to the contents of the third section [3], the fourth section [4], and the fifth section [5] in FIG. 13, the NO concentration is acquired by calculating the total concentration (the NO conversion value) based on the second current value Ip6, and more specifically, any one of the 100 ppm system, the 50 ppm system, and the 25 ppm system, acquiring the $NH_3$ concentration on the basis of the amount of change ΔIp, and subtracting the $NH_3$ concentration from the total concentration.

For example, in the case that the second current value Ip6 is 0.537 (μA), the fact that the total concentration is 25 ppm is calculated from the fifth section [5] of Table 1 of FIG. 13. In addition, in the case that the amount of change ΔIp is 0.041 (μA), the $NH_3$ concentration is 4.4 ppm from the fifth section [5] of Table 1 of FIG. 13. Accordingly, taking into consideration the difference in sensitivity between $NH_3$ and NO, the NO concentration is 25−4.4×1.14=approximately 20.0 ppm.

Moreover, in the case that no corresponding amount of change ΔIp exists on the map 110, the amount of change ΔIp that is closest thereto on the map may be specified to thereby calculate the total concentration, and together therewith, the $NH_3$ concentration may be determined, for example, by a known approximation calculation. In addition, the NO concentration may be determined by subtracting the determined $NH_3$ concentration from the calculated total concentration. Alternatively, the concentration of $NH_3$ which is the second target component may be calculated on the basis of a correlation equation between the respective concentrations of $NH_3$ and NO, ΔIp, and Ip6, and the concentration of NO which is the first target component may be calculated by subtracting the concentration of the second target component from the total concentration.

Next, a description will be given concerning an experimental example for the purpose of obtaining the map 110.

(1) The above-described first gas sensor 500A having the first sensor element 502A and the first protective cover 504A, and the second gas sensor 500B having the second sensor element 502B and the second protective cover 504B are manufactured, and the metal components are assembled into a sensor shape and attached to a model gas measurement apparatus. In addition, by the first heater 72A and the second heater 72B being incorporated into the first sensor element 502A and the second sensor element 502B, the first sensor element 502A and the second sensor element 502B are heated to approximately 850° C.

(2) The voltage applied between the first main interior side pump electrode 44A and the first exterior side pump electrode 46A, as well as the voltage applied between the second main interior side pump electrode 44B and the second exterior side pump electrode 46B are feedback-controlled, in a manner so that the electromotive force between the first auxiliary pump electrode 58A of the first sensor cell 15A and the first reference electrode 52A, and the electromotive force between the second auxiliary pump electrode 58B of the second sensor cell 15B and the second reference electrode 52B become 385 mV.

(3) Next, the voltage applied between the first auxiliary pump electrode 58A and the first exterior side pump electrode 46A, as well as the voltage applied between the second auxiliary pump electrode 58B and the second exterior side pump electrode 46B are feedback-controlled, in a manner so that the electromotive force between the first auxiliary pump electrode 58A of the first sensor cell 15A and the first reference electrode 52A, and the electromotive force between the second auxiliary pump electrode 58B of the second sensor cell 15B and the second reference electrode 52B become 380 mV.

(4) Furthermore, the voltage applied between the first measurement electrode 62A and the first exterior side pump electrode 46A, as well as the voltage applied between the second measurement electrode 62B and the second exterior side pump electrode 46B are feedback-controlled, in a manner so that the electromotive force between the first measurement electrode 62A of the first measurement pump cell 60A and the first reference electrode 52A in the first sensor cell 15A, and the electromotive force between the second measurement electrode 62B of the second measurement pump cell 60B and the second reference electrode 52B in the second sensor cell 15B, respectively, become 400 mV.

(5) Next, $N_2$ and 3% of $H_2O$ were made to flow as a base gas at 120 L/min to the model gas measurement apparatus, and upon having measured the current flowing to the first measurement pump cell 60A and the second measurement pump cell 60B, the offset current flowing to the first measurement pump cell 60A and the second measurement pump cell 60B was determined to be 0.003 μA.

(6) Next, while $N_2$ and 3% of $H_2O$ continued to flow as a base gas at 120 L/min to the model gas measurement apparatus, and while maintaining a total gas flow rate of 120 L/min, by the addition of $NH_3$ at amounts of 25, 50, 75, and 100 ppm, the first measurement pump current (first current value Ip3) and the second measurement pump current (second current value Ip6) flowing to the first measurement pump cell 60A and the second measurement pump cell 60B were measured (Experiment 1: refer to the first characteristic line L1 of FIG. 12, and the first section [1] of Table 1 of FIG. 13).

(7) Next, while $N_2$ and 3% of $H_2O$ continued to flow as a base gas at 120 L/min to the model gas measurement apparatus, and while maintaining a total gas flow rate of 120 L/min, by the stepwise addition of NO at amounts of 25, 50, 75, and 100 ppm, the first current value Ip3 and the second current value Ip6 flowing to the first measurement pump cell 60A and the second measurement pump cell 60B were measured (Experiment 2: refer to the second characteristic line L2 of FIG. 12, and the second section [2] of Table 1 of FIG. 13).

(8) Next, $N_2$ and 3% of $H_2O$ were made to flow as a base gas into the model gas measurement apparatus at 120 L/min, and the NO concentration was gradually reduced in a stepwise manner to NO=100, 80, 60, 40, 20, and 0 ppm, and with respect to each NO concentration of NO=80, 60, 40, 20, and 0 ppm, $NH_3$ was added to the gas, in a manner so as to maintain the second current value Ip6 of the second measurement pump cell 60B at the time that NO=100 ppm at 2.137 μA. At this time, the flow rate of the base gas was adjusted so as to maintain the total gas flow rate at 120 L/min. In each respective gas atmosphere, the first current value Ip3 flowing to the first measurement pump cell 60A was measured (Experiment 3). The relationship between the respective concentrations of NO and NH$_3$, the first current value Ip3 and the second current value Ip6, and the difference (amount of change ΔIp) between the first current value Ip3 and the second current value Ip6 is shown by the first plot group P1 of FIG. 12, and the third section [3] of Table 1 of FIG. 13.

(9) Next, N$_2$ and 3% of H$_2$O were made to flow as a base gas into the model gas measurement apparatus at 120 L/min, and the NO concentration was gradually reduced in a stepwise manner to NO=50, 40, 30, 20, 10, and 0 ppm, and with respect to each NO concentration of NO=40, 30, 20, 10, and 0 ppm, NH$_3$ was added to the gas, in a manner so as to maintain the second current value Ip6 of the second measurement pump cell 60B at the time that NO=50 ppm at 1.070 μA. At this time, the flow rate of the base gas was adjusted so as to maintain the total gas flow rate at 120 L/min. In each respective gas atmosphere, the first current value Ip3 flowing to the first measurement pump cell 60A was measured (Experiment 4). The relationship between the prespective concentrations of NO and NH$_3$, the first current value Ip3 and the second current value Ip6, and the difference (amount of change ΔIp) between the first current value Ip3 and the second current value Ip6 is shown by the second plot group P2 of FIG. 12, and the fourth section [4] of Table 1 of FIG. 13.

(10) Next, N$_2$ and 3% of H$_2$O were made to flow as a base gas into the model gas measurement apparatus at 120 L/min, and the NO concentration was gradually reduced in a stepwise manner to NO=25, 20, 15, 10, 5, and 0 ppm, and with respect to each NO concentration of NO=20, 15, 10, 5, and 0 ppm, NH$_3$ was added to the gas, in a manner so as to maintain the second current value Ip6 of the second measurement pump cell 60B at the time that NO=25 ppm at 0.537 μA. At this time, the flow rate of the base gas was adjusted so as to maintain the total gas flow rate at 120 L/min. In each respective gas atmosphere, the first current value Ip3 flowing to the first measurement pump cell 60A was measured (Experiment 5). The relationship between the respective concentrations of NO and NH$_3$, the first current value Ip3 and the second current value Ip6, and the difference (amount of change ΔIp) between the first current value Ip3 and the second current value Ip6 is shown by the third plot group P3 of FIG. 12, and the fifth section [5] of Table 1 of FIG. 13.

(11) Using the data obtained in Experiment 1 to Experiment 5, the map 110 shown in FIG. 12 was created. In order to confirm the certainty of the obtained map 110, the first current value Ip3 and the second current value Ip6 in the mixed gases of NO and NH$_3$ having concentrations that differ from each other in Experiments 1 to 5, and the difference (amount of change ΔIp) between the first current value Ip3 and the second current value Ip6 were measured, whereupon the results shown in Table 2 of FIG. 14 were obtained. When the results of Table 2 (indicated by Δ) were plotted on the graph of FIG. 12, the results were in good agreement with the concentrations estimated from the map 110.

Next, a gas sensor set (hereinafter referred to as a second gas sensor set 1000B) according to a second embodiment will be described further with reference to FIGS. 15 to 17B.

The second gas sensor set 1000B (see FIGS. 17A and 17B) has substantially the same configuration as the first gas sensor set 1000A described above, but differs therefrom in that a single gas sensor 500 in which the first sensor cell 15A and the second sensor cell 15B are integrated is used. Moreover, it should be noted that the members corresponding to the above-described first gas sensor set 1000A are designated by the same reference numerals, and duplicate description of such features is omitted.

Figure 15:
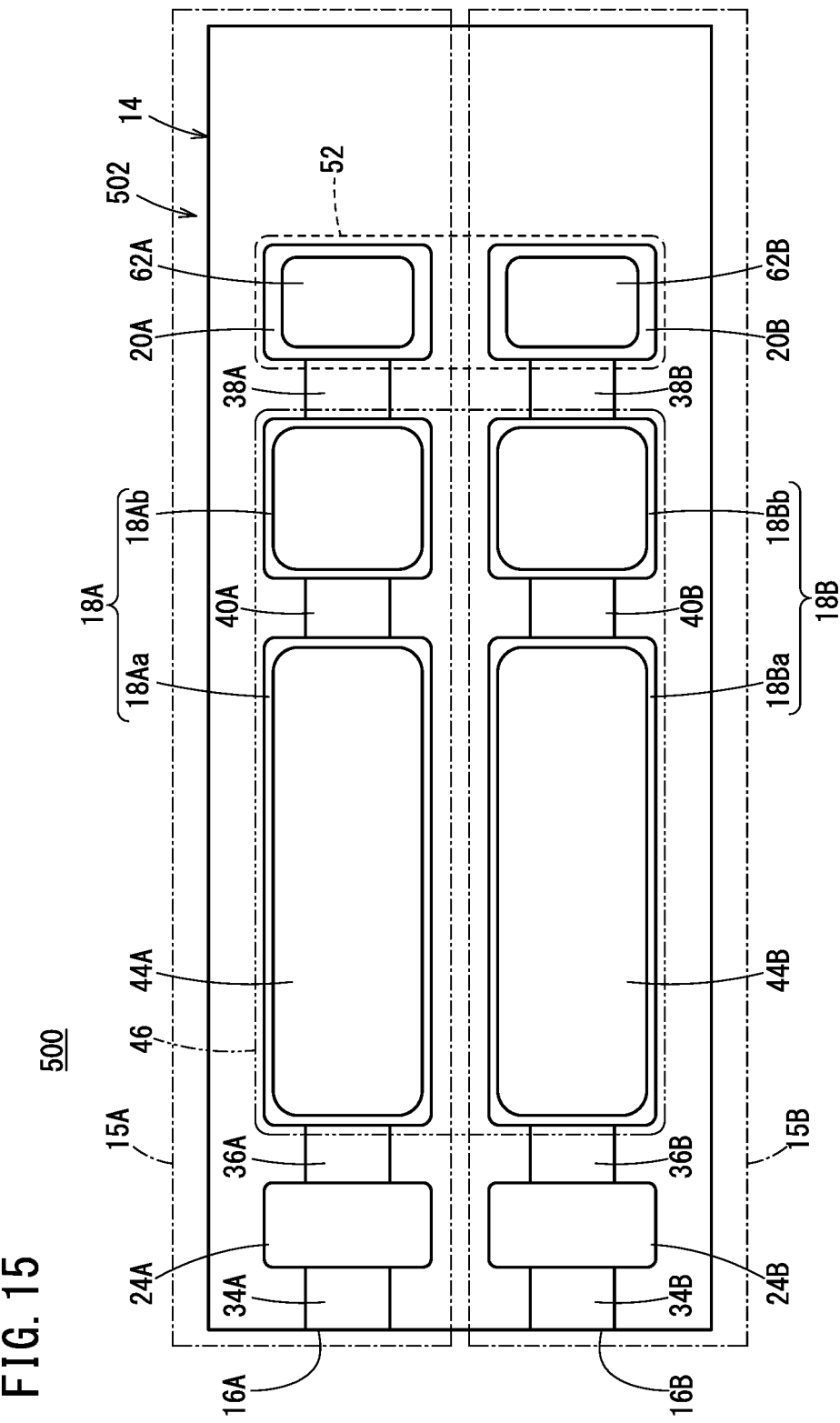
FIG. 15 is a cross-sectional view in which there is shown a structural example of a gas sensor that is used by the gas sensor set.

As shown in FIG. 15, the gas sensor 500 includes a single sensor element 502. The sensor element 502 includes a structural body 14 made up from an oxygen ion conductive solid electrolyte, and a first sensor cell 15A and a second sensor cell 15B formed in the structural body 14.

In this instance, when a thickness direction of the structural body 14 is defined as a vertical direction and a widthwise direction of the structural body 14 is defined as a horizontal direction, within one structural body 14, the first sensor cell 15A and the second sensor cell 15B are integrally disposed in a state of being aligned in the horizontal direction.

As shown in FIG. 15, the first sensor cell 15A includes a first gas introduction port 16A formed in the structural body 14 and into which a gas to be measured is introduced, a first oxygen concentration adjustment chamber 18A formed inside the structural body 14 and communicating with the first gas introduction port 16A, and a first measurement chamber 20A formed inside the structural body 14 and communicating with the first oxygen concentration adjustment chamber 18A. Since the configuration of these features is substantially the same as that of the first sensor cell 15A shown in FIGS. 7A and 8, duplicate description thereof will be omitted.

As shown in FIG. 15, the second sensor cell 15B includes a second gas introduction port 16B formed in the structural body 14 and into which a gas to be measured is introduced, a second oxygen concentration adjustment chamber 18B formed inside the structural body 14 and communicating with the second gas introduction port 16B, and a second measurement chamber 20B formed inside the structural body 14 and communicating with the second oxygen concentration adjustment chamber 18B. Since the configuration of these features is substantially the same as that of the second sensor cell 15B shown in FIGS. 7B and 9, duplicate description thereof will be omitted.

In addition, as shown in FIG. 15, a first exterior side pump electrode disposed on the outer side of at least the first oxygen concentration adjustment chamber 18A of the first sensor cell 15A, and a second exterior side pump electrode disposed on the outer side of at least the second oxygen concentration adjustment chamber 18B of the second sensor cell 15B are provided in common, thereby constituting a single exterior side pump electrode 46. Further, a reference electrode of the first sensor cell 15A and a reference electrode of the second sensor cell 15B are provided in common, thereby forming a single reference electrode 52.

Figure 16:
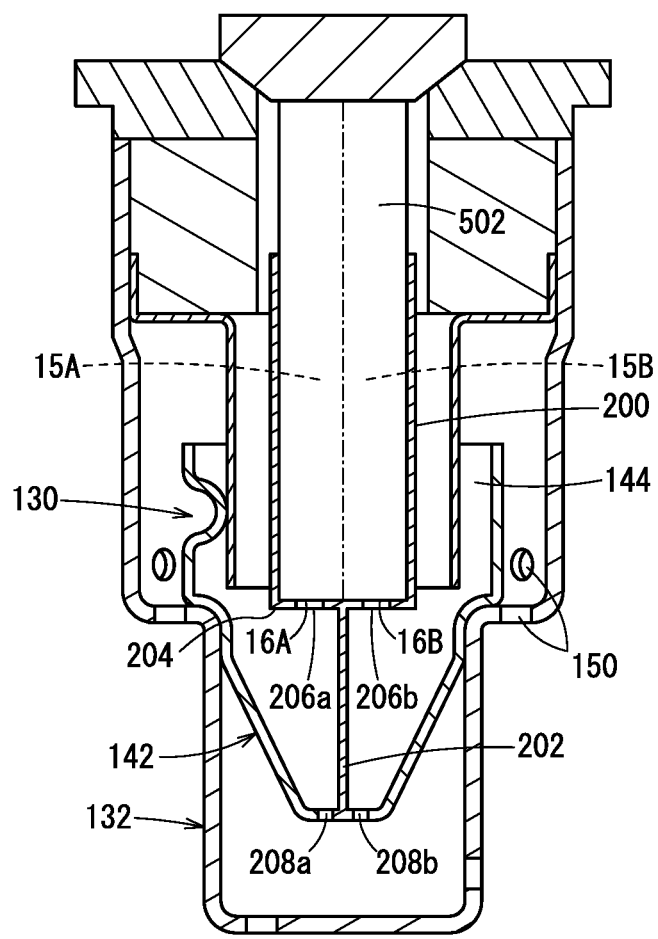
FIG. 16 is a vertical cross-sectional view showing a structural example of a protective cover corresponding to a gas sensor.

As shown in FIG. 16, in a protective cover 504 corresponding to the above-described gas sensor 500, there is provided a tubular retaining member 200 that retains the sensor element 502, and a partitioning member 202 provided between a central portion in a widthwise direction of a distal end portion of the retaining member 200, or stated otherwise, between an inner side cover 130 and a portion corresponding to a boundary between the first sensor cell 15A and the second sensor cell 15B. For example, a bottom plate 204 of the retaining member 200 is provided, and within the bottom plate 204, a first through hole 206a is provided in a portion corresponding to the first gas introduction port 16A of the first sensor cell 15A, and a second through hole 206b is provided in a portion corresponding to the second gas introduction port 16B of the second sensor cell 15B. Furthermore, the partitioning member 202 is disposed between the bottom plate 204 and an outer side member 142 of the inner side cover 130. Further, on the outer side member 142, there are provided a first through hole 208a corresponding to the first sensor cell 15A, and a second through hole 208b corresponding to the second sensor cell 15B. In addition, within the inner surface of the outer side member 142, a $NH_3$ oxidation catalyst is coated on an inner surface on the side of the first sensor cell 15A, and a $NH_3$ inert catalyst is coated on an inner surface on the side of the second sensor cell 15B.

Figure 17A:
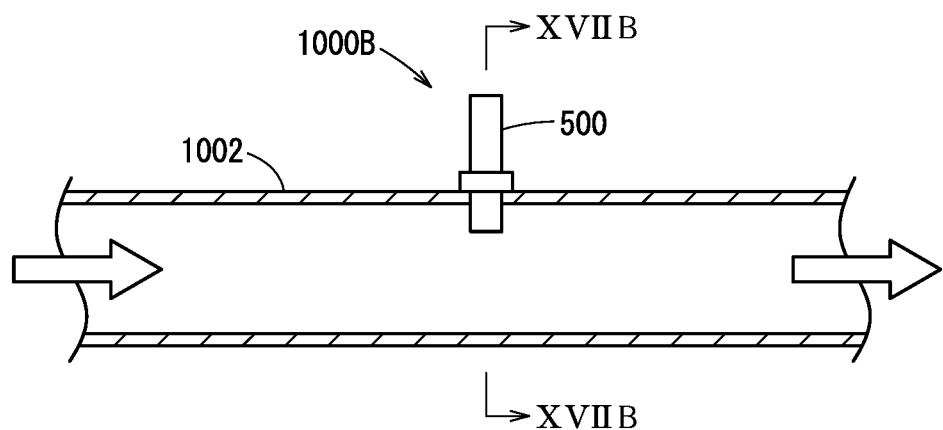
FIG. 17A is a schematic configuration diagram showing a second gas sensor set.
Figure 17B:
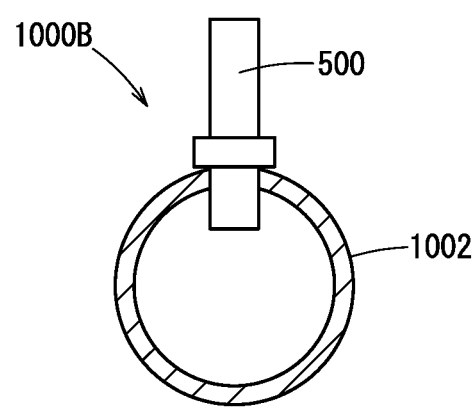
FIG. 17B is a cross-sectional view showing a structural example of the second gas sensor set (a cross-sectional view taken along line IB-IB in FIG. 1A: dashed lines omitted).

Due to the above-described configuration, the second gas sensor set 1000B produces the same advantageous effects as those of the first gas sensor set 1000A described above. In addition, in the gas sensor 500 of the second gas sensor set 1000B, the first sensor cell 15A and the second sensor cell 15B are integrated into one structural body 14. Therefore, as shown in FIGS. 17A and 17B, a single gas sensor 500 may be fixed to the exhaust pipe 1002, and the structure for attaching the gas sensor 500 to the exhaust pipe 1002 can be simplified. Moreover, since the exterior side pump electrode 46 is provided in common with the first sensor cell 15A and the second sensor cell 15B, and in the same manner, the reference electrode 52 is provided in common with the first sensor cell 15A and the second sensor cell 15B, it is possible to reduce the number of wirings.

[Inventions Obtained from the Embodiment]

A description will be given below concerning the inventions that can be grasped from the above-described embodiment.

[1] The first gas sensor set 1000A is a gas sensor set configured to detect a plurality of target components, and includes at least two gas sensors installed in the exhaust pipe 1002, wherein:

among the at least two gas sensors, the at least one first gas sensor 500A includes the first sensor element 502A including the first sensor cell 15A formed in the first structural body 14A made up from at least the oxygen ion conductive solid electrolyte;

among the at least two gas sensors, the at least one second gas sensor 500B includes the second sensor element 502B including the second sensor cell 15B formed in the second structural body 14B made up from at least the oxygen ion conductive solid electrolyte;

the oxidation catalyst for one target component from among a plurality of target components is coated over a range corresponding to at least the gas introducing portion of the first sensor element 502A; and the inert catalyst for the one target component is coated over a range corresponding to at least the gas introducing portion of the second sensor element 502B.

In accordance with such a configuration, it is possible to prevent both a decrease in the accuracy of calculating the concentrations due to lengthening of the switching cycle, and a decrease in the accuracy of calculating the concentrations due to low sensitivity. Further, it is possible to accurately measure the respective concentrations of a plurality of target components over a prolonged period, even under an atmosphere of a non-combusted component such as exhaust gas, and a plurality of target components (for example, NO and $NH_3$) that coexist in the presence of oxygen.

In addition, the oxidation catalyst for the one target component from among the plurality of target components is coated over a range corresponding to at least the gas introducing portion of the first sensor element 502A, and the inert catalyst for the one target component is coated over a range corresponding to at least the gas introducing portion of the second sensor element 502B. Therefore, merely by changing the software of the control system of the first gas sensor 500A and the second gas sensor 500B, the first gas sensor set 1000A is capable of easily realizing the process of measuring the respective concentrations of NO and $NH_3$ which heretofore could not be realized, without separately adding various measurement devices or the like as hardware. As a result, it is possible to improve the accuracy of controlling a NOx purification system and detecting failures thereof. In particular, it is possible to distinguish between NO and $NH_3$ in exhaust gas downstream of an SCR system, which contributes to precisely controlling the injected amount of urea, as well as detecting deterioration of the SCR system.

[2] In the first gas sensor set 1000A, there are further included the first protective cover 504A configured to protect at least the gas introducing portion of the first sensor element 502A, the first protective cover 504A including:

the first inner side member 140A disposed in surrounding relation to a side portion of the first sensor element 502A, and the first inner side cover 130A configured to cover at least the gas introducing portion of the first sensor element 502A; and the first outer side cover 132A configured to protect the first inner side cover 130A, to introduce the gas through the opening 150A, and to guide the gas rearwardly of the first inner side cover 130A;

wherein the first inner side cover 130A includes the rear opening 144A configured to guide the gas from the rear to the gas introducing portion of the first sensor element 502A.

In the first outer side cover 132A of the first protective cover 504A in the first gas sensor 500A, the gas is introduced through the opening 150A. The gas that is introduced into the first outer side cover 132A is guided rearwardly of the first inner side cover 130A, and is guided to the gas introducing portion of the first sensor element 502A through the rear opening 144A of the first inner side cover 130A. In particular, since the oxidation catalyst for the one target component is coated over a range corresponding to at least the gas introducing portion of the first sensor element 502A, the one target component contained within the gas that is guided to the gas introducing portion can be oxidized efficiently. In accordance with this feature, in combination with the inactive or inert action with respect to the one target component by the second protective cover 504B of the second gas sensor 500B, a contribution is made to the measurement of the respective concentrations, for example, of NO and $NH_3$.

[3] In the first gas sensor set 1000A, there is further included the second protective cover 504B configured to protect at least the gas introducing portion of the second sensor element 502B, the second protective cover 504B including the second inner side member 140B disposed in surrounding relation to the side portion of the second sensor element 502B, and the second inner side cover 130B configured to cover at least the gas introducing portion of the second sensor element 502B; and the second outer side cover 132B configured to protect the second inner side cover 130B, to introduce the gas through the opening 150B, and to guide the gas rearwardly of the second inner side cover 130B;

wherein the second inner side cover 130B includes the rear opening 144B configured to guide the gas from the rear to the gas introducing portion of the second sensor element 502B.

In the second outer side cover 132B of the second protective cover 504B, the gas is introduced through the opening 150B. The gas that is introduced into the second outer side cover 132B is guided rearwardly of the second inner side cover 130B, and is guided to the gas introducing portion of the second sensor element 502B through the rear opening 144B of the second inner side cover 130B. In particular, since the inert catalyst for the one target component is coated over a range corresponding to at least the gas introducing portion of the second sensor element 502B, the one target component contained within the gas that is guided to the gas introducing portion is maintained as it is without being oxidized. In accordance with this feature, in combination with the oxidizing action with respect to the one target component by the first protective cover 504A of the first gas sensor 500A, a contribution is made to the measurement of the respective concentrations, for example, of NO and NH$_3$.

[4] In the first gas sensor set 1000A, the first protective cover 504A includes:

the first inner side member 140A disposed in surrounding relation to the side portion of the first sensor element 502A, and having the plurality of through holes 160A in the rear part thereof;

the first inner side cover 130A configured to protect at least the gas introducing portion of the first sensor element 502A; and the first outer side cover 132A configured to protect the first inner side cover 130A, to introduce the gas through the opening 150A, and to guide the gas to the first inner side cover 130A;

wherein the first inner side cover 130A includes the diffusion piece 162A configured to cause the measurement gas, which has entered into the gap between the first outer side cover 132A and the first inner side member 140A, to be diffused or scattered, and to guide the measurement gas rearwardly of the first inner side member 140A.

In accordance with such a configuration, in the first outer side cover 132A of the first protective cover 504A in the first gas sensor 500A, the gas is introduced through the opening 150A. The gas that is introduced into the first outer side cover 132A is guided rearwardly of the first inner side member 140A by the diffusion piece 162A, and furthermore, is guided to the gas introducing portion of the first sensor element 502A through the plurality of through holes 160A of the first inner side member 140A. In particular, in the first protective cover 504A, since the oxidation catalyst for the one target component is coated over a range corresponding to at least the gas introducing portion of the first sensor element 502A, the one target component contained within the gas that is guided to the gas introducing portion can be oxidized efficiently. In accordance with this feature, in combination with the inactive or inert action with respect to the one target component by the second protective cover 504B of the second gas sensor 500B, a contribution is made to the measurement of the respective concentrations, for example, of NO and NH$_3$.

[5] In the first gas sensor set 1000A, the second protective cover 504B includes:

the second inner side member 140B disposed in surrounding relation to the side portion of the second sensor element 502B, and having the plurality of through holes 160B in the rear part thereof;

the second inner side cover 130B configured to protect at least the gas introducing portion of the second sensor element 502B; and the second outer side cover 132B configured to protect at least the second inner side cover 130B;

wherein the second inner side cover 130B includes a diffusion piece 162B configured to cause the measurement gas, which has entered into a gap between the second outer side cover 132B and the second inner side member 140B, to be diffused or scattered, and to guide the measurement gas rearwardly of the second inner side member 140B.

In accordance with such a configuration, in the second outer side cover 132B of the second protective cover 504B in the second gas sensor 500B, the gas is introduced through the opening 150B. The gas that is introduced into the second outer side cover 132B is guided rearwardly of the second inner side member 140B by the diffusion piece 162B, and furthermore, is guided to the gas introducing portion of the second sensor element 502B through a plurality of through holes 160B of the second inner side member 140B. In particular, in the second protective cover 504B, since the inert catalyst for the one target component is coated over a range corresponding to at least the gas introducing portion of the second sensor element 502B, the one target component contained within the gas that is guided to the gas introducing portion is maintained as it is without being oxidized. In accordance with this feature, in combination with the oxidizing action with respect to the one target component by the first protective cover 504A of the first gas sensor 500A, a contribution is made to the measurement of the respective concentrations, for example, of NO and NH$_3$.

[6] In the first gas sensor set 1000A, the oxidation catalyst, within the first protective cover 504A, is coated on at least the inner surface of the first inner side member 140A, or at least the inner surface of the first inner side cover 130A, or at least the inner surface of the first inner side member 140A and the inner surface of the first inner side cover 130A; and the inert catalyst, within the second protective cover 504B, is coated on at least the inner surface of the second inner side member 140B, or at least the inner surface of the second inner side cover 130B, or at least the inner surface of the second inner side member 140B and the inner surface of the second inner side cover 130B.

At least the gas introducing portion of the first sensor element 502A is exposed on the inner surface of the first inner side member 140A, and the inner surface of the first inner side cover 130A. Further, within the first protective cover 504A, the oxidation catalyst for the one target component is coated on at least the inner surface of the first inner side member 140A, or at least the inner surface of the first inner side cover 130A, or at least the inner surface of the first inner side member 140A and the inner surface of the first inner side cover 130A. Therefore, the one target component contained within the gas that is guided to the gas introducing portion can be oxidized efficiently.

At least the gas introducing portion of the second sensor element 502B is exposed on the inner surface of the second inner side member 140B, and the inner surface of the second inner side cover 130B. Further, within the second protective cover 504B, the inert catalyst for the one target component is coated on at least the inner surface of the second inner side member 140B, or at least the inner surface of the second inner side cover 130B, or at least the inner surface of the second inner side member 140B and the inner surface of the second inner side cover 130B. Therefore, the one target component contained within the gas that is guided to the gas introducing portion is maintained as it is without being oxidized.

[7] In the first gas sensor set 1000A, there is further provided the first temperature control device 100A configured to control the temperature of the first sensor cell 15A;

the second temperature control device 100B configured to control the temperature of the second sensor cell 15B;

the first oxygen concentration control device 102A and the second oxygen concentration control device 102B; and the target component concentration acquisition device 104;

wherein each of the first sensor cell 15A and the second sensor cell 15B is equipped, in a direction in which a gas is introduced, at least with the gas introduction port 16A (16B), the first diffusion rate control member 34A (34B), the first chamber (first diffusion resistance adjustment chamber 24A (second diffusion resistance adjustment chamber 24B)), the second diffusion rate control member 36A (36B), the second chamber (first oxygen concentration adjustment chamber 18A (second oxygen concentration adjustment chamber 18B)), the third diffusion rate control member 38A (38B), and the measurement chamber 20A (20B);

the measurement chamber 20A of the first sensor cell 15A includes the first measurement pump cell 60A;

the measurement chamber 20B of the second sensor cell 15B includes the second measurement pump cell 60B;

the first oxygen concentration control device 102A controls the oxygen concentration in the second chamber 18A of the first sensor cell 15A;

the second oxygen concentration control device 102B controls the oxygen concentration in the second chamber 18B of the second sensor cell 15B; and the target component concentration acquisition device 104:

acquires the concentration of the second target component, based on a difference between a current value flowing to the first measurement pump cell 60A and a current value flowing to the second measurement pump cell 60B;

acquires the total concentration of a first target component and the second target component, by the current value flowing to the second measurement pump cell 60B; and acquires the concentration of the first target component by subtracting the concentration of the second target component from the total concentration.

In accordance with such a configuration, it is possible to accurately measure the respective concentrations of a plurality of target components over a prolonged period, even under an atmosphere of a non-combusted component such as exhaust gas, and a plurality of target components (for example, NO and $NH_3$) that coexist in the presence of oxygen.

In addition, in the first gas sensor set 1000A, by coating the oxidation catalyst for the one target component on the first protective cover 504A and the like, coating the inert catalyst for the one target component on the second protective cover 504B and the like, and merely by changing the software of the control system of the first gas sensor 500A and the second gas sensor 500B, it is possible to easily realize the process of measuring the respective concentrations of NO and $NH_3$ which heretofore could not be realized, without separately adding various measurement devices or the like as hardware. As a result, it is possible to improve the accuracy of controlling a NOx purification system and detecting failures thereof. In particular, it is possible to distinguish between NO and $NH_3$ in exhaust gas downstream of an SCR system, which contributes to precisely controlling the injected amount of urea, as well as detecting deterioration of the SCR system.

[8] In the first gas sensor set 1000A, among the plurality of target components, one of the target components is $NH_3$, and the other of the target components is NO. In accordance with this feature, it is possible to distinguish between NO and $NH_3$ in exhaust gas downstream of an SCR system, which contributes to precisely controlling the injected amount of urea, as well as detecting deterioration of the SCR system.

[9] In the first gas sensor set 1000A, the target component concentration acquisition device 104 utilizes the map 110 in which there is specified the relationship between the NO concentration and the $NH_3$ concentration, respectively, by the current value Ip6, which is measured experimentally in advance, flowing to the second measurement pump cell 60B, and the difference ΔIp between the current value Ip3 flowing to the first measurement pump cell 60A and the current value Ip6 flowing to the second measurement pump cell 60B, and determines the respective concentrations of NO and $NH_3$ by comparing with the map 110 the current value Ip6 flowing to the second measurement pump cell 60B during actual use, and the difference ΔIp between the current value Ip3 flowing to the first measurement pump cell 60A and the current value Ip6 flowing to the second measurement pump cell 60B.

Merely by changing the software of the control system of the first gas sensor 500A and the second gas sensor 500B, the first gas sensor set 1000A is capable of easily realizing the process of measuring the respective concentrations of NO and $NH_3$ which heretofore could not be realized, without separately adding various measurement devices or the like as hardware.

[10] The second gas sensor set 1000B is a gas sensor set configured to detect a plurality of target components, and including the gas sensor 500 installed in the exhaust pipe 1002;

wherein the gas sensor 500 includes:

the structural body 14 made up from at least the oxygen ion conductive solid electrolyte;

the sensor element 502 including the first sensor cell 15A formed in the structural body 14 and having the first gas introducing portion, and the second sensor cell 15B formed in the structural body 14 and having the second gas introducing portion; and the protective cover 504 configured to protect at least the first gas introducing portion and the second gas introducing portion of the sensor element 502; and on the protective cover 504:

the oxidation catalyst for the one target component from among the plurality of target components is coated over a range corresponding to at least the first gas introducing portion of the sensor element 502; and the inert catalyst for the one target component is coated over a range corresponding to at least the second gas introducing portion of the sensor element 502.

In the second gas sensor set 1000B, aside from producing the same advantageous effects as those of the first gas sensor set 1000A described above, since the first sensor cell 15A and the second sensor cell 15B are integrated into one structural body 14, a single gas sensor 500 may be fixed to the exhaust pipe 1002, and the structure for attaching the gas sensor 500 to the exhaust pipe 1002 can be simplified. Moreover, the exterior side pump electrode 46 is provided in common with the first sensor cell 15A and the second sensor cell 15B, and in the same manner, since the reference electrode 52 can be provided in common with the first sensor cell 15A and the second sensor cell 15B, together with enabling a reduction in the size of the second gas sensor set 1000B, it is possible to reduce the number of wirings.

In the above-described second gas sensor set 1000B, the $NH_3$ oxidation catalyst may be coated on the inner side of the first gas introduction port 16A of the sensor element 502, and the $NH_3$ inert catalyst may be coated on the inner side of the second gas introduction port 16B.

[11] In the second gas sensor set 1000B:

the protective cover 504 includes the inner side cover 130 configured to protect at least the first gas introducing portion and the second gas introducing portion, and an outer side cover 132 configured to protect the inner side cover 130;

the inner side cover 130 includes the partitioning member 202 configured to separate the range corresponding to the first gas introducing portion and the range corresponding to the second gas introducing portion;

the oxidation catalyst, within the inner side cover 130, is coated over a range corresponding to the first gas introducing portion which is separated by the partitioning member 202; and the inert catalyst, within the inner side cover 130, is coated over a range corresponding to the second gas introducing portion which is separated by the partitioning member 202.

In accordance with such a configuration, within the gas that is introduced into the inner side cover 130, the one target component of the gas that is introduced over the range corresponding to the first gas introducing portion which is separated by the partitioning member 202 is oxidized by the oxidation catalyst. Similarly, within the gas that is introduced into the inner side cover 130, the one target component of the gas that is introduced over the range corresponding to the second gas introducing portion which is separated by the partitioning member 202 is maintained as it is without being oxidized.

In other words, on the inner side cover 130, by providing the partitioning member 202 that separates the range corresponding to the first gas introducing portion and the range corresponding to the second gas introducing portion, the gas sensor 500 in which the first sensor cell 15A and the second sensor cell 15B are integrated into the single structural body 14 can be provided with a function that is capable of detecting the one target component and the other target component.

[12] In the second gas sensor set 1000B, the protective cover 504 includes the inner side cover 130 configured to protect at least the first gas introducing portion and the second gas introducing portion, and the outer side cover 132 configured to protect the inner side cover 130; and the oxidation catalyst is coated on at least the first gas introducing portion (for example, the first gas introduction port 16A) of the sensor element 502, and the inert catalyst is coated on at least the second gas introducing portion (for example, the second gas introduction port 16B) of the sensor element 502.

Consequently, there is no need to provide the partitioning member 202 between the inner side cover 130 and the portion corresponding to the boundary between the first sensor cell 15A and the second sensor cell 15B, and the configuration can be simplified.

[13] In the second gas sensor set 1000B:

the inner side cover 130 includes the first opening 206a provided in a portion of a range corresponding to the first gas introducing portion, and the second opening 206b provided in a portion of a range corresponding to the second gas introducing portion;

the outer side cover 132 introduces the gas through the opening 150 from a substantially intermediate portion in a lengthwise direction, and guides the gas, within the inner side cover 130, rearwardly of the range corresponding to the first gas introducing portion, and rearwardly of the range corresponding to the second gas introducing portion; and the inner side cover 130 introduces the gas from the rear through the rear opening 144, guides the gas to the first gas introducing portion and the second gas introducing portion of the sensor element 502, and guides the gas through the first opening 206a and the second opening 206b to the side of the outer side cover 132.

In accordance with such a configuration, the gas, which is introduced toward the inner side cover 130 through the opening 150 of the outer side cover 132, is guided rearwardly of the range corresponding to the first gas introducing portion and rearwardly of the range corresponding to the second gas introducing portion.

The inner side cover 130 introduces the gas from respective rearward directions into the interior of the inner side cover 130 through the rear opening 144, and guides the gas to the first gas introducing portion and the second gas introducing portion of the sensor element 502. At this time, within the inner side cover 130, in the range corresponding to the first gas introducing portion that is separated by the partitioning member 202, the one target component of the introduced gas is oxidized, whereas in the range corresponding to the second gas introducing portion, the one target component of the introduced gas is maintained as it is without being oxidized. Consequently, it becomes possible to measure the concentrations, for example, of NO and $NH_3$. Moreover, the gas that is introduced into the interior of the inner side cover 130 is guided to the side of the outer side cover 132 through the first opening 208a and the second opening 208b provided in the inner side cover 130.

[14] In the method of measuring concentrations of a plurality of target components within the gas to be measured by the gas sensor set wherein:

the gas sensor set includes the first sensor cell 15A and the second sensor cell 15B;

each of the first sensor cell 15A and the second sensor cell 15B is equipped, in a direction in which the gas is introduced, at least with the gas introduction port 16A (16B), the first diffusion rate control member 34A (34B), the first chamber 24A (24B), the second diffusion rate control member 36A (36B), the second chamber 18A (18B), the third diffusion rate control member 38A (38B), and the measurement chamber 20A (20B);

the measurement chamber 20A of the first sensor cell 15A includes the first measurement pump cell 60A; and the measurement chamber 20B of the second sensor cell 15B includes the second measurement pump cell 60B;

the method including the steps of:

acquiring the concentration of the second target component, based on a difference between a current value flowing to the first measurement pump cell 60A and a current value flowing to the second measurement pump cell 60B;

acquiring a total concentration of the first target component and the second target component, by the current value flowing to the second measurement pump cell 60B; and acquiring a concentration of the first target component by subtracting the concentration of the second target component from the total concentration.

In accordance with such a configuration, it is possible to accurately measure the respective concentrations of a plurality of target components over a prolonged period, even under an atmosphere of a non-combusted component such as exhaust gas, and a plurality of target components (for example, NO and $NH_3$) that coexist in the presence of oxygen.

In addition, by coating the oxidation catalyst for the one target component on the first protective cover 504A and the like, coating the inert catalyst for the one target component on the second protective cover 504B and the like, and merely by changing the software of the control system of the first gas sensor 500A and the second gas sensor 500B, it is possible to easily realize the process of measuring the respective concentrations of NO and $NH_3$ which heretofore could not be realized, without separately adding various measurement devices or the like as hardware. As a result, it is possible to improve the accuracy of controlling a NOx purification system and detecting failures thereof. In particular, it is possible to distinguish between NO and $NH_3$ in exhaust gas downstream of an SCR system, which contributes to precisely controlling the injected amount of urea, as well as detecting deterioration of the SCR system.

In practicing the present invention, various configurations for improving reliability may be added as components for an automotive vehicle to such an extent that the concept of the present invention is not impaired.

What is claimed is:

1. A gas sensor set configured to detect a plurality of target components, and including at least two gas sensors installed in an exhaust pipe, wherein:
   among the at least two gas sensors, at least one first gas sensor comprises a first sensor element including a first sensor cell formed in a first structural body made up from at least an oxygen ion conductive solid electrolyte;
   among the at least two gas sensors, at least one second gas sensor comprises a second sensor element including a second sensor cell formed in a second structural body made up from at least an oxygen ion conductive solid electrolyte;
   an oxidation catalyst for one target component from among a plurality of target components is coated over a range corresponding to at least a gas introducing portion of the first sensor element;
   an inert catalyst for the one target component is coated over a range corresponding to at least a gas introducing portion of the second sensor element,
   wherein the gas sensor set further comprises a first protective cover configured to protect at least the gas introducing portion of the first sensor element,
   the first protective cover comprising:
   a first inner side cover configured to cover at least the gas introducing portion of the first sensor element, and
   wherein the oxidation catalyst is coated on at least an inner surface of the first inner side cover.

2. The gas sensor set according to claim 1,
   wherein the first inner side cover includes a first inner side member disposed in surrounding relation to a side portion of the first sensor element;
   the first protective cover further comprising:
   a first outer side cover, which includes a first outer side member and is configured to protect the first inner side cover, to introduce gas through an opening, and to guide the gas rearwardly of the first inner side cover,
   wherein the first inner side cover includes a rear opening configured to guide the gas from the rear to the gas introducing portion of the first sensor element.

3. The gas sensor set according to claim 1, further comprising a second protective cover configured to protect at least a gas introducing portion of the second sensor element, the second protective cover comprising:
   a second inner side member disposed in surrounding relation to a side portion of the second sensor element;
   a second inner side cover configured to cover at least the gas introducing portion of the second sensor element; and
   a second outer side cover configured to protect the second inner side cover, to introduce gas through an opening, and to guide the gas rearwardly of the second inner side cover;
   wherein the second inner side cover includes a rear opening configured to guide the gas from the rear to the gas introducing portion of the second sensor element.

4. The gas sensor set according to claim 2,
   wherein the first inner side member has a plurality of through holes in a rear part thereof, and
   wherein the first inner side cover includes a diffusion piece configured to cause a measurement gas, which has entered into a gap between the first outer side cover and the first inner side member, to be diffused or scattered, and to guide the measurement gas rearwardly of the first inner side member.

5. The gas sensor set according to claim 3, wherein the second protective cover comprises:
   a second inner side member disposed in surrounding relation to a side portion of the second sensor element, and having a plurality of through holes in a rear part thereof;
   a second inner side cover configured to protect at least the gas introducing portion of the second sensor element; and
   a second outer side cover configured to protect at least the second inner side cover,
   wherein the second inner side cover includes a diffusion piece configured to cause a measurement gas, which has entered into a gap between the second outer side cover and the second inner side member, to be diffused or scattered, and to guide the measurement gas rearwardly of the second inner side member.

6. The gas sensor set according to claim 2, wherein:
   the oxidation catalyst is coated on at least an inner surface of the first inner side member, or at least an inner surface of the first inner side member and an inner surface of the first inner side cover.

7. The gas sensor set according to claim 1, further comprising:
   a first temperature control device configured to control a temperature of the first sensor element;
   a second temperature control device configured to control a temperature of the second sensor element;
   a first oxygen concentration control device and a second oxygen concentration control device; and
   a target component concentration acquisition device;
   wherein each of the first sensor element and the second sensor element is equipped, in a direction in which a gas is introduced, at least with a gas introduction port, a first diffusion rate control member, a first chamber, a second diffusion rate control member, a second chamber, a third diffusion rate control member, and a measurement chamber;
   the measurement chamber of the first sensor cell comprises a first measurement pump cell; and
   the measurement chamber of the second sensor cell comprises a second measurement pump cell;
   the first oxygen concentration control device controls an oxygen concentration in the second chamber of the first sensor cell;
   the second oxygen concentration control device controls an oxygen concentration in the second chamber of the second sensor cell; and
   the target component concentration acquisition device:
   acquires a concentration of a second target component, based on a difference between a current value flowing to the first measurement pump cell and a current value flowing to the second measurement pump cell;

acquires a total concentration of a first target component and the second target component, by the current value flowing to the second measurement pump cell; and acquires a concentration of the first target component by subtracting the concentration of the second target component from the total concentration.

8. The gas sensor set according to claim 1, wherein, among the plurality of target components, one of the target components is $NH_3$, and another of the target components is NO.

9. The gas sensor set according to claim 8, wherein the target component concentration acquisition device:

utilizes a map in which there is specified a relationship between a NO concentration and a $NH_3$ concentration, respectively, by a current value, which is measured experimentally in advance, flowing to the second measurement pump cell, and a difference between a current value flowing to the first measurement pump cell and the current value flowing to the second measurement pump cell; and determines the respective concentrations of NO and $NH_3$ by comparing with the map the current value flowing to the second measurement pump cell during actual use, and the difference between the current value flowing to the first measurement pump cell and the current value flowing to the second measurement pump cell.

10. A gas sensor set configured to detect a plurality of target components, and including a gas sensor installed in an exhaust pipe;

wherein the gas sensor comprises:

a structural body made up from at least an oxygen ion conductive solid electrolyte;

a sensor element comprising a first sensor cell formed in the structural body and having a first gas introducing portion, and a second sensor cell formed in the structural body and having a second gas introducing portion; and a protective cover configured to protect at least the first gas introducing portion and the second gas introducing portion of the sensor element; and on the protective cover:

an oxidation catalyst for one target component from among the plurality of target components is coated over a range corresponding to at least the first gas introducing portion of the sensor element; and an inert catalyst for the one target component is coated over a range corresponding to at least the second gas introducing portion of the sensor element, the protective cover comprising:

an inner side cover configured to cover at least the gas introducing portion of the first sensor cell; and wherein the oxidation catalyst, within the protective cover, is coated on at least an inner surface of the inner side cover.

11. The gas sensor set according to claim 10, wherein:

the protective cover includes an outer side cover configured to protect the inner side cover;

the inner side cover includes a partitioning member configured to separate a range corresponding to the first gas introducing portion and a range corresponding to the second gas introducing portion;

the oxidation catalyst, within the inner side cover, is coated over a range corresponding to the first gas introducing portion which is separated by the partitioning member; and the inert catalyst, within the inner side cover, is coated over a range corresponding to the second gas introducing portion which is separated by the partitioning member.

12. The gas sensor set according to claim 10, wherein:

the protective cover includes an outer side cover configured to protect the inner side cover wherein the oxidation catalyst is coated on at least the first gas introducing portion of the sensor element, and the inert catalyst is coated on at least the second gas introducing portion of the sensor element.

13. The gas sensor set according to claim 11, wherein:

the inner side cover includes a first opening provided in a portion of the range corresponding to the first gas introducing portion, and a second opening provided in a portion of the range corresponding to the second gas introducing portion;

the outer side cover introduces a gas through an opening from a substantially intermediate portion in a lengthwise direction, and guides the gas, within the inner side cover, rearwardly of the range corresponding to the first gas introducing portion, and rearwardly of the range corresponding to the second gas introducing portion; and the inner side cover introduces the gas from the rear through a rear opening, guides the gas to the first gas introducing portion and the second gas introducing portion of the sensor element, and guides the gas through the first opening and the second opening to a side of the outer side cover.

14. A method of measuring concentrations of a plurality of target components within a gas to be measured by a gas sensor set wherein:

the gas sensor set comprises a first sensor cell and a second sensor cell;

each of the first sensor cell and the second sensor cell is equipped, in a direction in which a gas is introduced, at least with a gas introduction port, a first diffusion rate control member, a first chamber, a second diffusion rate control member, a second chamber, a third diffusion rate control member, and a measurement chamber;

the measurement chamber of the first sensor cell comprises a first measurement pump cell, the measurement chamber of the second sensor cell comprises a second measurement pump cell, an oxidation catalyst for one target component from among a plurality of target components is coated over a range corresponding to at least a gas introducing portion of the first sensor cell, and an inert catalyst for the one target component is coated over a range corresponding to at least a gas introducing portion of the second sensor cell, the gas sensor set further comprises a protective cover configured to protect at least the gas introducing portion of the first sensor cell, the protective cover comprising:

a first inner side cover configured to cover at least the gas introducing portion of the first sensor element, and the oxidation catalyst, within the first protective cover, is coated on at least an inner surface of the first inner side cover, the method comprising the steps of:

acquiring a concentration of a second target component, based on a difference between a current value flowing to the first measurement pump cell and a current value flowing to the second measurement pump cell;

acquiring a total concentration of the first target component and a second target component, by the current value flowing to the second measurement pump cell; and acquiring a concentration of the first target component by subtracting the concentration of the second target component from the total concentration.

15. The gas sensor set according to claim 3, wherein:
the inert catalyst is coated on at least an inner surface of the second inner side member, or at least an inner surface of the second inner side cover, or at least an inner surface of the second inner side member and an inner surface of the second inner side cover.

* * * * *